US006514760B1

(12) United States Patent
Mao et al.

(10) Patent No.: US 6,514,760 B1
(45) Date of Patent: Feb. 4, 2003

(54) JOINTLESS GENE OF TOMATO

(75) Inventors: Long Mao, Clemson, SC (US); Rod A. Wing, Central, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 09/611,659

(22) Filed: Jul. 7, 2000

(51) Int. Cl.$^7$ .................. C12N 15/29; C12N 15/82; C07H 21/04
(52) U.S. Cl. ............ 435/419; 435/320.1; 536/23.6
(58) Field of Search ............ 435/320.1, 419, 435/468; 536/23.6; 800/278, 298

(56) References Cited

PUBLICATIONS

Doerks, TIG, Jun. 1998, TIG vol. 14 No. 6, pp248–250.*
"Investigation of Jointless Candidate Gene", (Jul. 27–31, 1996), Plant Physiology (Rockville), vol. III., No. 2 Suppl., 1996, p. 144 by Cheung et al.
"Molecular Cloning of SVP: A Negative Regulator of the Floral Transition in Arabidopsis", (Feb. 2000), vol. 21, No. 4, pp. 351–360 by Hartmann et al.
EMBL Database Accession No. AI895411.
EMBL Database Accession No. AI489275.
"*JOINTLESS* is a MADS–box gene controlling tomato flower abscission zone development"; L. Mao, D. Begum, H–w. Chuang, M.A. Budiman, E.J. Szymkowiak, E.E. Irish, R.A. Wing; Nature 406, 910–913, Aug. 24, 2000.
"A Deep–Coverage Tomato BAC Library and Prospects Toward Development of an STC Framework for Genome Sequencing"; M.A. Budiman, L. Mao, T. Wood, R.A. Wing; Genome Research 10, 129–136; Nov. 1999.
"Genetic mapping of *jointles*–2 tomato chromosome 12 using RFLP and RAPD markers"; H.–B. Zhang, M.A. Budiman, R.A. Wing; Theor Appl Genet 100, 1183–1189; Oct. 1999.
"Interactions between *jointless* and Wild–Type Tomato Tissues during Development of the Pedicel Abscission Zone and the Inflorescense Meristem"; E.J. Szymkowiak, E.E. Irish; The Plant Cell 11, 159–175; Feb. 1999.
"Map–based cloning in crop plants: tomato as a model system II. Isolation and characterization of a set of overlapping yeast artificial chromosomes encompassing the *jointless* locus"; H.–B. Zhang, G.B. Martin, S.D. Tanksley, R.A. Wing; Mol Gen Genet 244, 613–621; Mar. 1994.
"Map–based cloning in crop plants. Tomato as a model system: I. Genetic and physical mapping of *jointless*"; R.A. Wing, H.–B. Zhang, s.D. Tanksley; Mol Gen Genet 242, 681–688; Sep. 1993.
"Flower abscission in mutant tomato plants"; G.A. Tucker, B.S. Schindler, J.A. Roberts; Planta 160, 164–167; 1984.
"Inherited Characters in the Tomato. II. Jointless Pedicel"; L. Butler; J Hered 37, 25–26; 1936.

* cited by examiner

*Primary Examiner*—Elizabeth F. McElwain
*Assistant Examiner*—Cynthia Collins
(74) *Attorney, Agent, or Firm*—Womble, Carlyle, Sandridge & Rice, PLLC

(57) ABSTRACT

The present invention relates to the isolation and identification of a JOINTLESS gene from a tomato plant (genus Lycopersicon). More specifically, the invention relates to novel nucleic acid molecules isolated from a tomato plant, proteins encoded by such nucleic acid molecules, and antibodies raised against such proteins. The present invention is also directed to a nucleic acid homolog of a JOINTLESS gene and a method to identify a homolog in plants other than tomato.

17 Claims, 13 Drawing Sheets

```
acttatcctagaattattttgagataacttattttccgttcaaacgaatt
gtggtcgtgaaaaatattcgtttatcaatacactattggtaaattgtat
atcaagtatctaccttctgaaggtgttgcatacatattcccttttaaa
ctttacttcggtatcatgttattgtatattgtttatgtaaagggacaaca
aaagttagggctaatcgagttcagtaattttgactcaaatatgatattt
gtgggttaaattttttatgaatatttattatcgaaagtagaagtcttt
gtacggatttgaatgaaccaaatatctttagttcatatctttgtattggt
atttagaatactcataaatatgtacatttttttttaattcaaaacctcg
ttactaaccettgatgttgttatcttaaaatttagaacgtatacgtaata
tttaaatttcaactctgttctataggttccaccttcatgttctaaatttat
aacccataatacataaatttaaaattctgagtccgtttctgatattatat
ttttttttcatcttatttgttttttaaatgtcaggctaccttactcaggct
gaagagatcaaaagcaaggtgtggctattttgtatgttattagaagaag
gagaaaaaaaaagtaactactaattattataattaattaatgtctgatt
aatgtaaaagctaaccccaaaaatttcatattatgtatgtaattggtgta
ttaatctcatgtattcgtctcccatagtttatataaatattattgttagt
atctattaacttaattaactagcactaataatctttataattgaacttt
gtgacttgtaactatataaaggcttaattatttaattatttgactttttt
ctgttgctgtaaatttaaatatttacttggtgacggtaaactatacttct
atctatattcagtgttgaacattagttatttgaaatttttagtggatgat
ttataatatgttattgtaagaataatttaatttaattttttgaatcattt
ccgtatctagcactaattaatttgtagtccttatcatgttcatatttaat
agttgaagacatgcataaaaacaattcaattacttgagtttcattttcaa
accattaggttgtatatgtttcttatccaaattataataaatcatttata
gaaattttaacacaattattatgtgtgtacgtttttaattttttttaatc
aaaatacaccttaactataaggagtgtgagctttctaaactatttaccaa
aacacatttcaactatcaaatgtaccgatttttttatctaaaataggaa
aaaacttacccgcagaatgtttacatcaaagtcaatgcaatttccgttat
tatgtaatttaatgaagtaaaatgaataataaatttcaacacatgacata
catatattgacagtgtaaatcttcgacgtggttttaccctaaaatatta
tcatcatttgagtaaaagataacaatattcgatacttgatatacctttt
aaaaaaatcaaaactgttgcaaagaaagctcagaatataagaagaaagg
acaagaagtataagatagaggagataattttcttattcaagtatgtatta
caaaaggtgaatgatatctctatttatagagttgagatatcaccccaaaa
gcccccatgataaatgtccaattagtaggtacatagttatccaaatgatt
cttatcaccttgggaacatgtatacatgaatacaattaagtcttgagtaa
atctaaaggataatccacacaatccaatggatttataacacttccccttg
gatgtccatagattatgtgcctcgttaaaaccttactaggaaaaacccag
t
```

*Fig. 2A*

```
ccctcttttat aaattccctc tttcttcat aactctctta gttctatttt
tggaaaattaa aaaaaaaaaa actcctaat ggctagagaa aaaattcaga
tcaagaaaata gataactcca cagcaagac aagttacatt ttcaaagagg
agaagaggttt attcaagaaa gctgaagaa ctttctgttc tctgtgatgc
tgatgttgctc tcatcatttt ctcttctac tggaaaatta tttgactatt
ctagctcaagc atgaaacaaa ttcttgaga ggcgtgattt gcattccaaa
aatctggaaaa attggatcaa ccatcactt gaacttcagc ttgtagaaaa
tagcaactact ccagattaag caaggaaat ttccgaaaaa agtcatcgat
taaggcaaatg aggggagaag aacttcaag gactaaatat tgaagagttg
caacaattgga gagatctctt gaaactgga ttgagccgcg tcatagagag
aaagggtgata aataatgag agagatcaa ccaactccaa caaaagggta
tgcatctaatg gaagaaaatg aaaaattaa ggcaacaggt gatggagata
tctaataataa taataataat aataatgga tatagagagg caggagtagt
aatatttgaac cagaaaatgg atttaataa taataataat gaagatggcc
aatcatctgaa tcagtaacaa atccatgta actcaattga tcctcctcct
caagatgatga tagttctgat acttctctc aaattggggt tagctaccttt
actcaggctga agagatcaaa agcaaggtg tggctatttt tgtatgttat
tagaagaagga gaaaaaaaaa agtaactac taattattat aattaattaa
tgtctgattaa tgtaaaagct aaccccaaa aatttcatat tatgtatgta
attggtgtatt aatctcatgt attcgtctc ccatagttta tataaatatt
attgttagta
```

*Fig. 2B*

```
atg gct aga gaa aaa att cag atc aag aaa ata gat aac tcc aca aga caa gtt aca
ttt tca aag agg gct aga ggt tta ttc tct aag aaa gct gaa gaa ctt aga ctc ctc tgt gat
gct gat gtt gct ctc att ctt gag agg ctt tct act gat cat gga aaa tct tct gac tat agc tca
agc atg aaa caa ctt gaa cag cag ctt gta gaa aat ttg cat aga aaa aat ctg aaa aat ttg gat
caa cca tca gaa agt cat caa gag cga tta gaa aga tct ctt aga agc ctt caa gga cta aat
att tcc gaa gag ttg caa caa ata tta atg gag aga gaa aac tcc gga gaa tac agc gtc ata gag
att gaa ggt gat aaa gaa tat aga gag cag caa ggt gta gaa caa ctg cgc atg cat cta
aga aag ggt gat aat gga tat aga gag gca gga ata cag gta aat tct aat aag ggt aat aat aat
atg gaa gaa aat aat gaa gat gat gat ggc caa aag ata ata tct gaa cca gaa aat ttg aat
aat aat aat aat cct cct caa gat gat aaa gag atg ata ttt aaa caa aat cca aat tgg aac tca att
gat cct cct agg ctg aag aga tca aaa aga agt tct act gat gta aca aaa aaa tct ctc tat gct acc
tta ctc agg aaa aag taa gca agg tgt ggc tgt ttt tgt atg tta tta gaa gaa
gga gaa aaa aag
```

```
6001 TTTTTTTCAT CTTATTTGTT TTTTAAATGT CAGgctacct tactcaggct gaagagatca aaagcaaggt gtggctattt ttgtatgtta ttagaagaag
                                            A  T  L  L  R  L   K  R  S   K  A  R   C  G  Y  F   C  M  L    L  E  E
6101 gagaaaaaa aaagtaacta ctaattatta atgtctgatt aatgtaaaag ctaacccaa aaattcata ttatgtatgt aattggtgta
      G  E  K  K  *
6201 ttaatctcat gtattcgtct cccatagttt atataaatat tattgttagt aTCTATTAAC TTAATTAACT AGCACTAATA ATCTTTTATA ATTGAACTTA
6301 GTGACTTGTA ACTATATAAA GGCTTAATTA TTTAATTATT TGACTTTTTT CTGTTGCTGT AAATTAAAT ATTTACTTGG TGACGGTAAA CTATACTTCT
6401 A
```

*Fig. 6B*

JOINTLESS GENE OF TOMATO

FIELD OF THE INVENTION

The present invention relates to the identification of a JOINTLESS gene from a tomato plant (genus Lycopersicon). More specifically, the invention relates to novel nucleic acid molecules isolated from a tomato plant, proteins encoded by such nucleic acid molecules, and antibodies raised against such proteins. The present invention is also directed to a nucleic acid homolog of a JOINTLESS gene and a method to identify a homolog.

BACKGROUND OF THE INVENTION

The present invention relates to the JOINTLESS gene, a new MADS-box gene in a distinct phylogenetic group separate from those functioning in floral organs. A deletion in the JOINTLESS gene is likely responsible for the failure to activate the pathway for development of the pedicel abscission zone in jointless tomato plants (genus Lycopersicon). The invention further relates to the identification of novel nucleic acid molecules, or degenerate variants thereof, and polypeptides encoded by such nucleic acid molecules that suppress the formation of flower and fruit pedicel abscission zones in tomato.

The publications cited herein to clarify the background of the invention and in particular, materials cited to provide additional details regarding the practice of the invention, are incorporated herein by reference, and for convenience are cited in the following text.

Abscission is a universal and dynamic process occurring in the plant kingdom whereby fruit, flowers, and leaves are shed during both the normal course of development and in response to tissue damage and stress. Abscission occurs in plants at a morphologically distinct region called the abscission zone (AZ). Like some other members of the Solanaceae family such as potato, the AZ in the tomato is formed in the middle of the pedicel and is easily visualized as an indentation or "joint" consisting of five to ten tiers of unexpanded cells transversing the pedicel (Roberts et al., *Planta* 160: 159–163, 1984, the content of which is incorporated herein by reference in its entirety). Jointed plants shed flowers and fruit at the abscission zone while often retaining the distal parts of pedicels and calyxes.

Although much is known about the physiological process of abscission at fully developed AZ, the mechanism regulating the development of the AZ is not yet fully understood (reviewed by Sexton and Roberts, *Ann Rev Plant Physiol* 33: 133, 1982, the content of which is incorporated herein by reference in its entirety).

In tomato, the jointless (j) and jointless-2 (j2) mutations (L. Butler, *J. Hered*. 37: 25, 1936 and C. M. Rick, *Am J Bot*, 43: 687, 1956 respectively) completely suppress the formation of pedicel AZ. The jointless (j) and Jointless-2 (j2) mutations have been genetically mapped to chromosome 11 and chromosome 12 respectively (L. Butler, *J Hered* 37: 25, 1936; Rick and Yoder, *Annu Rev Genet* 22: 281, 1988 and Zhang et al., *Theor Appl Genet*, in press, respectively). Both simple recessive mutations, jointless also affects determinate growth: inflorescence meristems revert to vegetative growth after forming only one or two flowers, resulting in a "leafy" inflorescence phenotype (Rick and Sawant, *Am Soc Hort Sci* 66: 354, 1955 and Pnueli et al., *Development* 125: 1979, 1998). In addition to its biological significance in providing a means to study AZ development, jointless has agronomic value. Since there is no region on the pedicel at which the jointless plant can shed its flowers or fruit, unfertilized flowers shrivel and die on the pedicels and fruit remains on the plant until manually harvested. This latter property is useful in the tomato processing industry because the final product is a stemless tomato fruit, which aids in mechanical harvesting.

Accordingly, it has become increasingly important to identify and isolate the JOINTLESS gene to enable modification of flower and fruit abscission in plants. Additionally, the identification and isolation of the JOINTLESS gene in tomato will enable homologous genes in other plant species to be identified and isolated, especially in those species in which the creation of a jointless or abscission zone-free line would be economically advantageous such as cotton, oil rape seed and soybean.

SUMMARY OF THE INVENTION

The present invention relates to the isolation and identification of novel nucleic acid molecules, and degenerate variants thereof, and to the proteins encoded by such nucleic acid molecules which relate to the development and formation of flower and fruit pedicel and peduncle AZs. In particular, the compositions of the present invention include novel nucleic acid molecules, including recombinant DNA molecules, cloned genes or degenerate variants thereof, especially variants occurring naturally, which encode JOINTLESS gene products. The nucleic acid sequence of the tomato JOINTLESS gene (also referred to as 240K4.12) is also provided.

The compositions of the present invention further include cloning vectors, including expression vectors, containing the nucleic acid molecules of the present invention, and hosts transformed with the nucleic acid molecules of the present invention. The present invention also contemplates methods for identifying and isolating genes homologous to the JOINTLESS gene in plants other than tomato.

Other aspects of the present invention include expression vectors designed to express the protein coded for by the JOINTLESS gene, plant lines transformed to carry the JOINTLESS gene, host cells transformed to express proteins encoded by JOINTLESS gene, and antibodies specifically reactive to those proteins.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which:

FIG. 2 shows the nucleotide sequence of JOINTLESS, with the genomic DNA sequence (SEQ ID NO: 1) depicted in FIG. 2A; the cDNA coding region including the 3' and 5' non-coding region (SEQ ID NO: 2) depicted in FIG. 2B; and the cDNA coding region alone (SEQ ID NO: 3) depicted in FIG. 2C.

FIG. 3 shows the nucleotide sequence of the JOINTLESS coding region (SEQ ID NO: 3) with the corresponding 3-letter amino acid designation listed below its respective nucleotide triplet.

FIG. 6 schematically illustrates JOINTLESS. FIG. 6A is a schematic of the wild-type JOINTLESS gene, while FIG. 6B depicts the genomic sequence of JOINTLESS, with the one-letter amino acid designation listed above its corresponding nucleotide triplet in the coding region.

DETAILED DESCRIPTION OF PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used in another embodiment to yield a still further embodiment. It is intended that the present invention covers such modifications and variations as come within the scope of the appended claims and their equivalents.

This description uses gene nomenclature accepted by the Cucurbit Genetics Cooperative as it appears in the *Cucurbit Genetics Cooperative Report* 18:85, 1995; herein incorporated by reference in its entirety. Using this gene nomenclature, genes are symbolized by italicized Roman letters. If a mutant gene is recessive to the normal type, then the symbol and name of the mutant gene appear in italicized lower case letters.

Figure 1A:
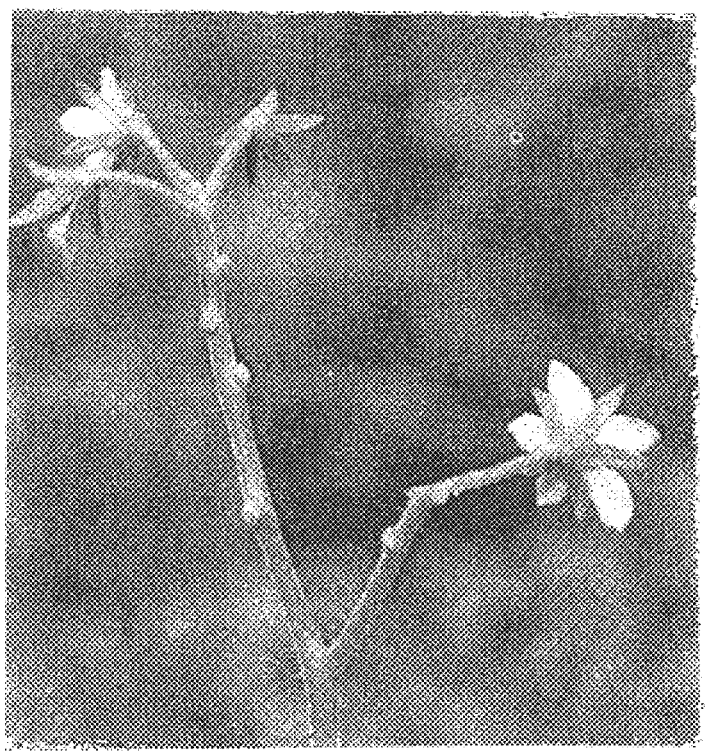
FIGS. 1A and 1B are photographs comparing a tomato plant exhibiting a "jointed" phenotype (FIG. 1A) with one exhibiting the "jointless" phenotype (FIG. 1B).
Figure 1B:
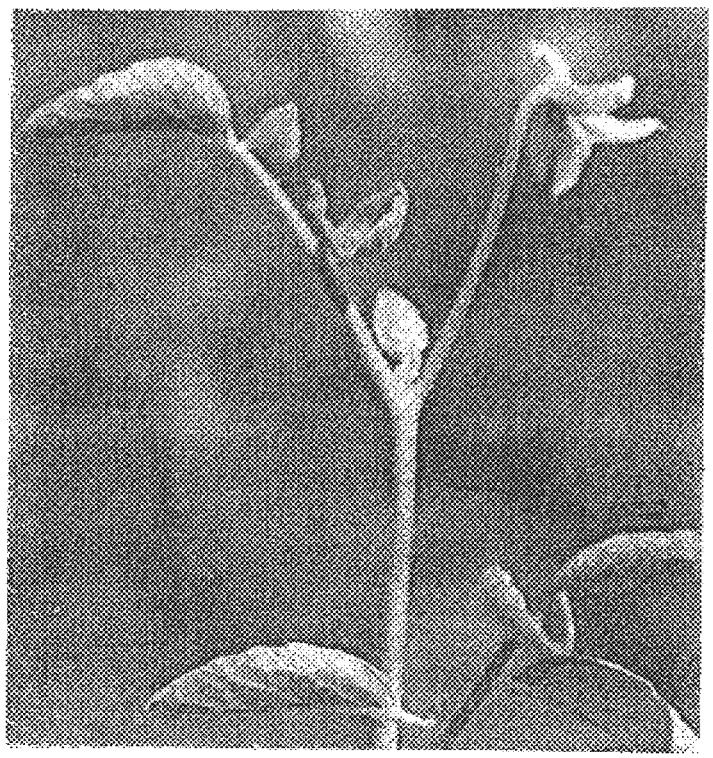

The present invention relates to the identification and isolation of a JOINTLESS gene from tomato (genus Lycopersicon), a new MADS-box gene in a distinctive phylogenetic lade separate from those functioning in floral organs. As shown in FIG. 1A, the abscission zone (AZ) in the tomato is formed in the middle of the pedicel as an indentation or "joint" and is easily visualized. The jointless mutation suppresses AZ formation completely, as shown in FIG. 1B, and results in a plant that can not shed its flowers or fruit.

For purposes of this specification, the term "gene" or "genes" is used to mean nucleic acid sequences (including both RNA or DNA) that encode genetic information for the synthesis of a whole RNA, a whole protein, or any portion of such whole RNA or whole protein. Genes that are not part of a particular plant's genome are referred to as "foreign genes" and genes that are a part of a particular plant's genome are referred to as "endogenous genes". The term "gene product" refers to RNAs or proteins that are encoded by the gene. "Foreign gene products" are RNA or proteins encoded by foreign genes and "endogenous gene products" are RNA or proteins encoded by endogenous genes.

As used herein the terms "polypeptide" and "protein" are used interchangeably, and refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a mammal, or are synthesized.

The term "nucleic acid" is intended to mean natural and synthetic linear and sequential arrays of nucleotides and nucleosides, for example cDNA, genomic DNA, mRNA, RNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors such as expression, cloning, cosmid and transformation vectors (for example, pBR322, lambda and the like), plant viral vectors (modified TMV, tobamovirus, and the like), and synthetic oligonucleotides like chemically synthesized DNA or RNA.

As used herein, the term expression vector may further include at least one regulatory sequence operably linked to the nucleotide sequence coding for the JOINTLESS protein. Regulatory sequences are well recognized in the art and may be selected to ensure good expression of the linked nucleotide sequence without undue experimentation by those skilled in the art. As used herein, the term regulatory sequences includes promoters, enhancers, and other elements which may control expression. Standard molecular biology textbooks such as *"Molecular Cloning: A Laboratory Manual,"* 2nd ed., J. Sambrook et al., eds. (Cold Spring Harbor Press, 1989) and *Methods in Plant Molecular Biology: A Laboratory Course Manual*, P. Maliga et al., eds. (Cold Spring Harbor Press, 1994) may be consulted to design suitable expression vectors, promoters, and other expression control elements. It should be recognized, however, that the choice of a suitable expression vector depends upon multiple factors including the choice of the host cell to be transformed and/or the type of protein to be expressed.

The term "isolated nucleic acid" is used to mean a nucleic acid with a structure not identical to that of any naturally occurring nucleic acid or to that of any fragment of a naturally occurring genomic nucleic acid spanning more than three separate genes, and includes DNA, RNA, or derivatives thereof. The term covers, for example, (a) a DNA which has the sequence of part of a naturally occurring genomic molecule but is not flanked by both of the coding sequences that flank that part of the molecule in the genome of the plant in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), ligase chain reaction (LCR) or chemical synthesis, or a restriction fragment; and (d) a recombinant nucleotide sequence that is part of a hybrid gene, i.e., a gene encoding a fusion protein. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a JOINTLESS protein of the present invention.

The term "fragment" when used to refer to a nucleic acid (e.g., cDNA) is used herein to mean a portion of the subject nucleic acid constructed artificially (e.g., by chemical synthesis) or by cleaving a natural product into multiple pieces (e.g., using restriction endonucleases).

The term "antisense DNA" is used to mean a gene sequence DNA that has a nucleotide sequence homologous to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example, that encoded by an antisense DNA or synthesized complementary with the antisense DNA). Antisense RNA is capable of hybridizing under stringent conditions with an antisense DNA. The antisense RNA of the invention is useful for inhibiting expression of a "target gene" either at the transcriptional or translational level. For example, transcription of the subject nucleic acids may produce antisense transcripts that are capable of inhibiting transcription by inhibiting initiation of transcription or by competing for limiting transcription factors; or, the antisense transcripts may inhibit transport of the "target RNA", or, the antisense transcripts may inhibit translation of "target RNA".

The term "sense strand" is used to mean the single stranded DNA molecule from a genomic DNA that is transcribable and translatable into the polypeptide product of the gene. The term "antisense strand" is used to mean the single strand DNA molecule of a genomic DNA that is complementary with the sense strand of the gene.

The term "capable of hybridizing under stringent conditions" is used to mean annealing a first nucleic acid to a second nucleic acid under stringent conditions (defined below). Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample, and the second nucleic acid may be the sense or antisense strand of a JOINTLESS gene. Hybridization of the first and second nucleic acids is conducted under stringent conditions, e.g., high temperature and/or low salt content, which tend to disfavor hybridization of dissimilar nucleotide sequences. A suitable hybridization protocol involving hybridization in 6×SSC, at 65 degrees Celsius in aqueous solution, followed by washing with 1×SSC at 65 degrees Celsius. Formulae to calculate appropriate hybridization and wash conditions to achieve hybridization permitting 30% or less mismatch between two nucleic acid molecules are disclosed, for example, in Meinkoth et al., *Anal Biochem* 138: 267–284, 1984; the content of which is herein incorporated by reference in its entirety. Protocols for hybridization techniques are well known to those of skill in the art and standard molecular biology manuals may be consulted to select a suitable hybridization protocol without undue experimentation. See, for example, *Molecular Cloning: A Laboratory Manual*, 2nd ed., J. Sambrook et al., eds. (Cold Spring Harbor Press, 1989; the content of which is herein incorporated by reference in its entirety).

As used herein, the term "encoding" is used to mean that the subject nucleic acid may be transcribed and translated into the subject protein in a cell as, for example, by linking the subject nucleic acid to appropriate control elements such as promoters and enhancers in a suitable vector (e.g., an expression vector) and introducing the vector into a cell.

The term "antibody" is used to refer to polyclonal and monoclonal antibodies and fragments thereof, and immunologic binding equivalents thereof, which are capable of specifically binding to the JOINTLESS polypeptides and fragments thereof, including epitopes thereof, or to polynucleotide sequences from the JOINTLESS region, particularly from the JOINTLESS locus or a portion thereof. The term "antibody" refers to a homogeneous molecular entity, or a mixture such as a serum product made up of a plurality of different molecular entities.

The present invention also provides for isolated JOINTLESS nucleic acid molecules. As used herein, a JOINTLESS nucleic acid molecule includes nucleic acid sequences related to a natural tomato JOINTLESS gene and includes all regions such as regulatory regions that control production of the JOINTLESS protein encoded by the gene (such as, but not limited to, transcription, translation or post-translation regulatory sequences) as well as the coding region itself, and any introns or non-translated coding regions. As used herein, a gene that "comprises" or includes a sequence may include that sequence as one contiguous sequence, or may include the sequence as separate exons. As used herein, the term "coding region" refers to a continuous linear arrangement of nucleotides which is translated into a protein. A full length coding region is translated into a full length protein; that is, a complete protein as would be translated in its natural state absent any post-translational modifications In one embodiment, a JOINTLESS gene of the present invention includes the nucleic acid sequence corresponding to the genomic sequence for JOINTLESS (SEQ ID NO: 1) as described in the Examples below. As used herein "genomic sequence" refers to the total DNA in the genome of an organism, and includes non-coding regions like introns.

In another embodiment, a tomato JOINTLESS gene or nucleic acid molecule can be an allelic variant of SEQ ID NO: 1. An allelic variant is a gene that occurs essentially at the same locus or loci in the plant genome as the gene including SEQ ID NO: 1, but which has a similar, but not identical, sequence to that of SEQ ID NO: 1. As used herein, the term "locus" or "loci" is used to mean the site of a gene on a chromosome. Hereditary traits are controlled by pairs of genes, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

One embodiment of the present invention is an isolated nucleic acid molecule comprising a JOINTLESS nucleic acid molecule (SEQ ID NO: 1) or a degenerate variant thereof. The identifying characteristics of such nucleic acid molecules are heretofore described. A nucleic acid molecule of the present invention can include an isolated deletion mutation corresponding to the jointless phenotype, a natural JOINTLESS gene, a JOINTLESS cDNA molecule, a degenerate variant thereof and/or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybridazation product (i.e., hybridization under stringent hybridization conditions) with the complementary sequence of another nucleic acid molecule. As such, the minimal size of a nucleic acid molecule of the present invention is from about 15 to about 18 nucleotides in length. Preferred nucleic acid molecules of the present invention include: a) an isolated JOINTLESS genomic DNA (SEQ ID NO: 1), the sequence of which is shown in FIG. 2A; b) a JOINTLESS cDNA molecule including 3' and 5' non-coding regions (SEQ ID NO: 2), the sequence of which is shown in FIG. 2B; c) a JOINTLESS cDNA molecule encompassing the coding region alone (SEQ ID NO: 3), the sequence of which is depicted in FIG. 2C; and/or nucleic acid molecules representing degenerate variants thereof. Such nucleic acid molecules can include nucleotides in addition to those included in SEQ ID NO: 1, SEQ ID NO: 2, and SEQ ID NO: 3, such as, but not limited to, a full-length gene, a full-length coding region, or a nucleic acid molecule encoding a fusion protein.

A nucleic acid molecule of the present invention also includes allelic variants and nucleic acid homologues, as well as nucleic acid molecules modified by nucleotide substitutions, deletions, additions and/or inversions in such a way that such modifications do not substantially interfere with the nucleic acid's ability to encode a JOINTLESS protein of the present invention. As used herein, a homolog also encompasses a gene from a different genus or species than a gene of interest, but which has a similar function to the gene of interest while having a nucleotide sequence not identical to that of the gene of interest. For example, a homolog of JOINTLESS would function in a species other than tomato in a similar manner to produce a JOINTLESS protein, but would not have a sequence identical to JOINTLESS.

A JOINTLESS nucleic acid molecule homolog or modification can be produced using a number of methods known to those skilled in the art. Suitable protocols can be found in conventional molecular biology manuals such as *Molecular Cloning: A Laboratory Manual*, 2nd ed., J. Sambrook et al., eds. (Cold Spring Harbor Press, 1989); the content of which is incorporated by reference herein in its entirety. For example, nucleic acid molecules can be modified using a variety of techniques including, but not limited to, classic mutagenesis and recombinant DNA techniques. The present invention is meant to include natural allelic variants as well as nucleic acid homologs resulting from the application of techniques such as restriction enzyme cleavage, ligation of nucleic acid fragments, PCR amplification, RT-PCR amplification, site-directed mutagenesis, chemical synthesis of nucleic acid molecules including, but not limited to oligonucleotide primers and mixtures thereof and combinations thereof. Nucleic acid molecule homologs can be selected by hybridization with a JOINTLESS gene or JOINTLESS nucleic acid molecule of the present invention or by screening the function of a protein encoded by the nucleic acid molecule.

In one embodiment of the present invention, a cDNA nucleic acid molecule of the present invention includes a nucleic acid that is at least about 75%, preferably at least about 80%, more preferably at least about 85%, even more preferably at least about 90%, and even more preferably at least about 95% identical to a nucleic acid molecule as depicted in SEQ ID NO: 2, and/or an allelic variant of such a nucleic acid molecule.

In another embodiment of the present invention, a cDNA nucleic acid molecule of the present invention includes a nucleic acid that is at least about 75%, preferably at least about 80%, more preferably at least about 85%, even more preferably at least about 90%, and even more preferably at least about 95% identical to a nucleic acid molecule as depicted in SEQ ID NO: 3, and/or an allelic variant of such a nucleic acid molecule.

Knowing the nucleic acid sequence of a JOINTLESS nucleic acid molecule of the present invention allows one skilled in the art to, for example, (a) make copies of those nucleic acid molecules, (b) obtain nucleic acid molecules which include at least a portion of such nucleic acid molecules (e.g., nucleic acid molecules including full-length genes, full-length coding regions, regulatory control sequences, truncated coding regions and the like), and (c) obtain JOINTLESS nucleic acid homologs in plants such as cotton and oil rape seed. Such nucleic acid homologs can be obtained in a variety of ways including by screening appropriate expression libraries with antibodies of the present invention; using traditional cloning techniques employing oligonucleotide probes made according to the present invention to screen appropriate libraries; amplifying appropriate libraries or DNA using oligonucleotide primers of the present invention in a polymerase chain reaction or other amplification method; and screening public and/or private databases containing genetic sequences using nucleic acid molecules of the present invention to identify targets. Examples of preferred libraries to screen, or from which to amplify nucleic acid molecules, include but are not limited to tomato BAC libraries, genomic DNA libraries, and cDNA libraries. Similarly, preferred sequence databases useful for screening to identify sequences in other species homologous to JOINTLESS include, but are not limited to, GenBank and the tomato Gene Index database of The Institute of Genomics Research (TIGR).

Figure 3:
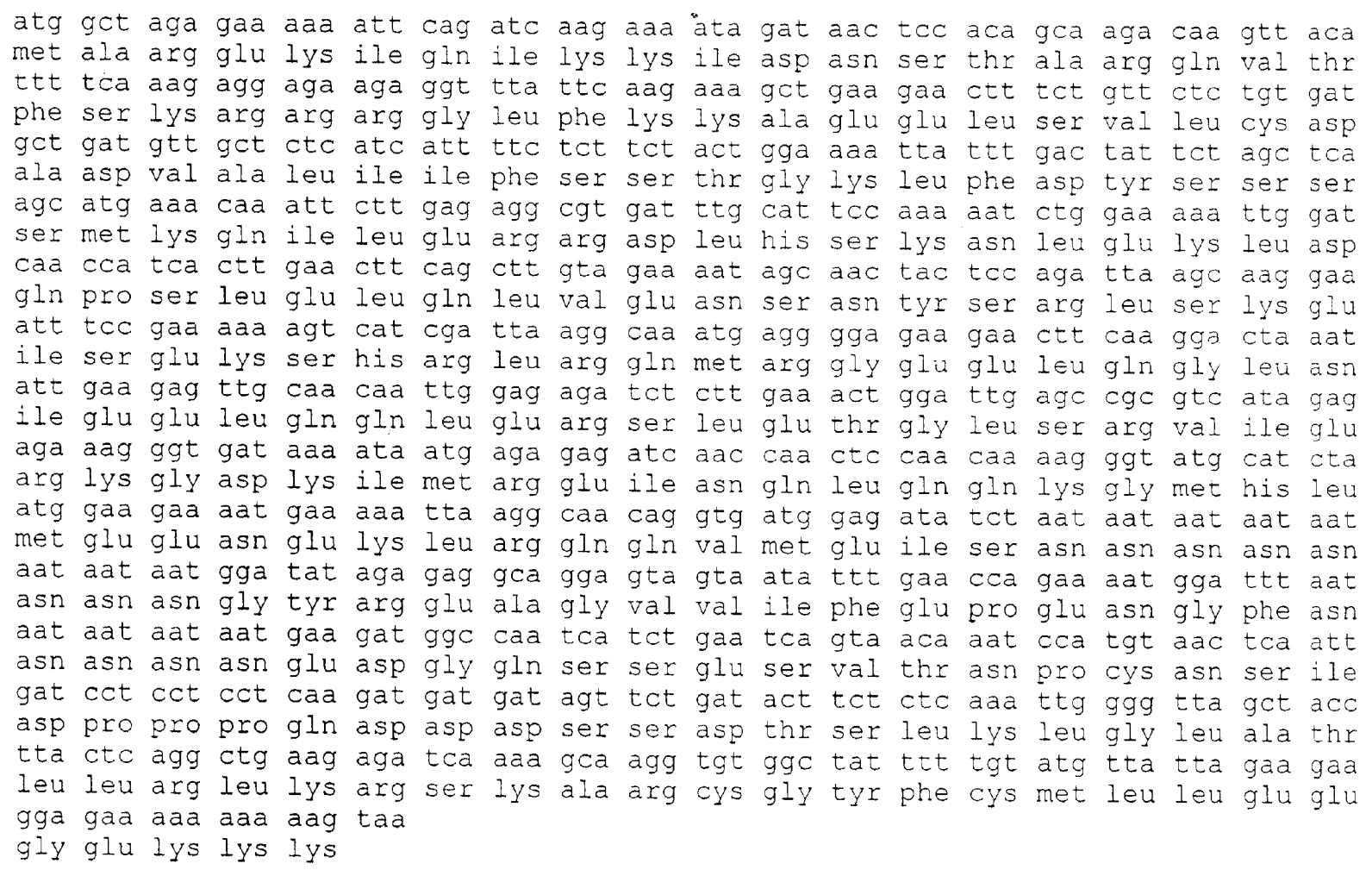

An isolated nucleic acid molecule of the present invention can include a nucleic acid sequence that encodes at least one protein of the present invention, examples of such proteins being disclosed herein. For example, FIG. 3 illustrates a nucleic acid sequence according to the present invention (SEQ ID NO: 3) and a corresponding JOINTLESS protein (SEQ ID NO: 4) coded for by that nucleic acid and contemplated to be within the scope of the present invention. The amino acid sequence of the JOINTLESS protein is depicted in FIG. 3 as its 3-letter code, with each amino acid listed above its corresponding nucleotide triplet.

Contemplated within the scope of the present invention is a JOINTLESS protein having an amino acid sequence as depicted in SEQ ID: 4 or a substantial similarity thereto. Isolated proteins of the present invention include the entire protein as depicted in SEQ ID: 4, as well as a protein fragment, a protein analogue, or an immunologic fragment thereof.

In another embodiment of the present invention, a JOINTLESS nucleic acid molecule of the present invention encodes a protein having an amino acid sequence that is at least about 75%, preferably at least about 80%, more preferably at least about 85%, even more preferably at least about 90%, and even more preferably at least about 95% identical to a JOINTLESS protein whose amino acid sequence is disclosed in SEQ ID NO: 4, as well as allelic variants of a JOINTLESS nucleic acid molecule encoding a protein having these sequences, including nucleic acid molecules that have been modified to accommodate codon usage properties of the cells in which such nucleic acid molecules are to be expressed.

The present invention further includes a host cell transformed to express a JOINTLESS protein. A recombinant expression vector suitable for transformation of a host cell means that the recombinant expression vector contains a nucleic acid molecule, or an oligonucleotide fragment thereof, of the present invention coupled to a regulatory sequence selected on the basis of the host cell used for expression. For example, the nucleic acid sequence coding for the JOINTLESS protein of the present invention may be operatively linked to a regulatory sequence selected to direct expression of the desired protein in an appropriate host cell.

The recombinant expression vectors of the present invention can be designed for the expression of the encoded proteins in prokaryotic or eukaryotic cells. For example, prokaryotic expression systems include *E. coli*—the most common expression system used. Useful *E. coli* vectors may contain constitutive or inducible promoters to direct expression of either fusion or non-fusion proteins. With fusion vectors, a number of amino acids are usually added to the expressed target gene sequence at the amino terminus. Additionally, a proteolytic cleavage site may be introduced at a site between the target recombinant protein and the fusion sequence. Once the fusion protein has been purified, the cleavage site allows the target recombinant protein to be separated from the fusion sequence. Enzymes suitable for use in cleaving the proteolytic cleavage site include Factor Xa and thrombin. Fusion expression vectors which may be useful in the present invention include pGex (Amrad Corp., Melbourne, Australia), pRIT5 (Pharmacia, Piscataway, N.J.) and pMAL (New England Biolabs, Beverly, Mass.), which fuse glutathione S-transferase, protein A, or maltose E binding protein, respectively, to the target recombinant protein.

Expression of unfused foreign genes in *E. coli* may be accomplished with recombinant vectors including, but not limited to, the *E. coli* expression vector pUR278 (Ruther et al., *EMBO J.* 2:1791,1983). Using the pUR278 vector, the nucleotide sequence coding for the JOINTLESS gene product may be ligated in frame with the lac V coding region to produce a fusion protein. Other useful vectors include pin vectors (Inouye and Inouye, *Nucleic Acids Res.* 13:3101–3109, 1985) and the like.

Expression of a foreign gene can also be obtained using eukaryotic vectors such as mammalian, yeast or insect cells. The use of eukaryotic vectors permits partial or complete glycosylation and/or the formation of the relevant inter- or intra-chain disulfide bonds. Examples of vectors useful for expression in the yeast *Saccharomyces cerevisiae* include pYepSecl (Baldari et al. *EMBO* 6:229–234, 1987) and pYES2 (Invitrogen Corp., San Diego, Calif.).

Baculovirus vectors are also available for the expression of proteins in cultured insect cells (F9 cells). The use of recombinant Baculovirus vectors can be, or is, analogous to the methods disclosed in "Baculovirus Expression Protocol", ed. by C. D. Richardson, 1995, Humana Press Inc.; Smith et al., "Production of Human Beta Interferon in Insect Cells Infected with a Baculovirus Expression Vector," *Mol Cellular Biol* 3:2156–2165, 1983; Pennock et al., Strong and Regulated Expression of *Escherichia coli* B-Galactosidase in Insect cells with a Baculovirus Vector, *Mol Cellular Biol* 4:399–406, 1984.

Other vectors useful for expressing the JOINTLESS protein, or an epitope of a JOINTLESS protein, include viral vectors. As used herein, the term "epitope" refers to a part of the protein that specifically binds an antibody by fitting into the antibody-combining site. Methods for making a viral recombinant vector useful for expressing the JOINTLESS protein are analogous to the methods disclosed in U.S. Pat. Nos. 4,603,112; 4,769,330; 5,174,993; 5,505,941; 5,338,683; 5,494,807; 4,722,848; E. Paoletti, "Applications of Poxvirus Vectors to Vaccination: An Update," *PNAS USA* 93:11349–11353, 1996; Moss, "Genetically Engineered Poxviruses for Recombinant Gene Expression, Vaccination and Safety," *PNAS USA* 93:11341–11348, 1996; Roizman, "The Function of Herpes Simplex Virus Genes: A Primer for Genetic Engineering of Novel Vectors," *PNAS USA* 93:11307–11302, 1996; Frolov at al., "Alphavirus-Based Expression Vectors: Strategies and Applications," *PNAS USA* 93:11371–11377, 1996; Grunhaus et al., "Adenoviruses As Cloning Vectors," Seminars in Virology 3: 237–252, 1993 and U.S. Pat. Nos. 5,591,639; 5,589,466; and 5,580,859 relating to DNA expression vectors, inter alia; the contents of which are incorporated herein by reference in their entirety.

Another aspect of the present invention pertains to the use of an isolated nucleic acid molecule for constructing nucleotide probes and primers useful for a variety of functions. For example, synthetic oligonucleotide probes are useful for detecting complementary nucleotide sequences in biological materials such as cells, cell extracts or tissues (as well as in an in situ hybridization technique). For example, isolated nucleic acids synthesized according to the present invention can determine whether a cell expresses an mRNA transcript encoding the JOINTLESS protein. The present invention also contemplates the use of antisense nucleic acid molecules, which are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths—the number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

Nucleotides constructed in accordance with the present invention can be labeled to provide a signal as a means of detection. For example, radioactive elements such as $^{32}$P, $^{3}$H, and $^{35}$S or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide*, 2nd Edition, 1991 (Promega Corp., Madison, Wis.; the content of which is incorporated herein in its entirety) may be consulted to select an appropriate labeling protocol without undue experimentation.

The present invention also pertains to the production and use of an antibody specifically reactive with a JOINTLESS protein. The antibody may be monoclonal or polyclonal and may be produced by conventional methodology using the JOINTLESS protein, or an immunologic fragment thereof, as an immunogen. For example, a mammal (i.e., a mouse, rabbit, horse, sheep, or goat) may be immunized with a JOINTLESS protein of the present invention, or an immunogenic fragment thereof, using an immunization protocol conducive to producing antibodies reactive with the JOINTLESS protein. Following completion of the immunization steps, antiserum reactive with the jointed protein may be collected and, if desired, polyclonal anti-JOINTLESS antibodies isolated.

Alternatively, monoclonal antibodies may be produced using procedures well known to those with skill in the art. Briefly, spleen cells are harvested from an immunized mouse and fused with immortalizing cells (i.e., myeloma cells) to yield antibody-producing hybridomas. The hybridomas can be screened immunochemically for production of monoclonal antibodies specifically reactive with the JOINTLESS protein. Protocols for producing, isolating and purifying conventional and monoclonal antibodies may be analogous to those described in Cassone et al., Production and Characterization of a Monoclonal Antibody to a Cell Surface Glucomannoprotein Constituent of *Candida albicans* and Other Pathogenic Candida Species, *J Med Microbiol* 27:233–238, 1988; D. C. Hancock and G. I. Evan, Production and Characterization of Antibodies against Synthetic Peptides, pgs. 23–33 in *Immunochemical Protocols*, ed. M. M. Manson, 1992 (Humana Press, Totowa, N.J.); Goding, J. W., Monoclonal Antibodies: Principles and Practice, 2d ed., 1986 (Academic Press Ltd., London) and J. F. Lam and L. M. Mutharia, "Antigen-Antibody Reactions," pgs. 104–132 in *Methods for General and Molecular Bacteriology*, ed. P. Gerhardt, 1994 (ASM Press, Washington, D.C.)(the contents of which are incorporated herein by reference in their entirety). Commercial sources for obtaining custom polyclonal antisera and monoclonal antibodies are also available. For example, HTI Bio-Products, Inc. (Ramona, Calif.) produces custom-made antibodies, antisera, ascites fluid and hybridoma lines.

An antibody made according to the present invention can be used to detect the JOINTLESS protein in cells, cell extracts, or in other biological preparations which can contain the JOINTLESS protein. Additionally, such an antibody can be labeled with a detector molecule to allow for detection of an antigen/antibody complex. Suitable labels include various enzymes, fluorescent molecules, radioactive labels, chemiluminescent molecules and the like. For example, enzymes useful for labeling antibodies include horseradish peroxidase and alkaline phosphatase. Fluorescent labels include, but are not limited to, fluorescein, rhodamine, dansyl chloride or phycoerythrin. Radioactive labels include, but are not limited to, $^3$H, $^{32}$P and $^{35}$S.

The present invention is further illustrated by the following examples, which are provided by way of illustration and should not be construed as limiting. The contents of all references, published patents and patents cited throughout the present application are hereby incorporated by reference in their entirety.

EXAMPLE 1

Plant Materials

*L. esculentum* near isogenic lines LA3023 (jointless homozygote j/j) and LA3021 (jointed homozygote J/J) were provided by Dr. C. Rick, Tomato Genetics Stock Center, University of California at Davis, USA.

EXAMPLE 2

DNA Isolation

The DNA isolation procedure is as follows: Approximately 3 g young leaf tissue was harvested, placed in a manila envelope, and frozen at −80 degrees Celsius as soon as possible. Subsequently, the samples were immersed in liquid nitrogen, ground to a fine powder, and the resulting powder transferred to 50 ml screw cap centrifuge tubes. The tubes were stored at −80 degrees Celsius until ready to use. When extracting DNA, each frozen leaf sample was added to 20–25 ml cold Extraction Buffer (0.35 M Sorbitol; 0.1 M Tris-base; 0.005 M EDTA, pH adjusted to 7.5 with HCl). Just before use, sodium bisulfite (0.02 M=3.8 g/liter) was added to the Extraction Buffer and the samples were homogenized for 5–10 seconds at room temperature. The samples were then centrifuged in a Beckman GS-6R table-top centrifuge at full speed for 20 minutes. After the supernatant was decanted, 1.25 ml of the Extraction Buffer was added and the suspension vortexed at full speed for 5 seconds. After vortexing, 1.75 ml Nuclear Lysis Buffer (200 ml of 1.0 M Tris; 200 ml of 0.25 M EDTA; 400 ml of 5.0 M NaCl; 20 g of CTAB added to 200 ml of ddH20) and 0.6 ml 5% Sarkosyl was added to each tube. Tubes were capped, inverted 5–10 times, and incubated at 65 degrees Celsius for 20 minutes. Following the incubation step, 7.5 ml chloroform/isoamyl alcohol (24:1) was added to each tube. The tubes were capped, placed on an orbital shaker for 20–30 minutes, and centrifuged (Beckman GS-6R) at full speed for 15–20 minutes. The aqueous supernatant was carefully pipetted off into 15 ml Falcon tubes and the DNA precipitated by adding 4 ml cold isopropanol to each tube. The tubes were capped, inverted 5–10 times, and the DNA was hooked out. The DNA was dried on a Kimwipe, resuspended in 100–300 ul TE for 10 min at 65 degrees Celsius, and centrifuged in a tabletop centrifuge at medium speed for 10 minutes. The DNA was stored at −20 degrees Celsius before use.

EXAMPLE 3

Genetic and Physical Mapping

Genetic mapping: Plant DNA for restriction fragment length polymorphism (RFLP) analysis was isolated as described in Example 2. RFLP analysis was performed as previously described (Tanksley et al., *Genetics* 132:1141–1160, 1992, the content of which is incorporated herein by reference in its entirety). Linkage data was analyzed using the Mapmaker (version 1.0) program for Macintosh computers using the Kosambi mapping function (Kosambi, D., *Ann Eugen* 12: 172–175, 1944; the content of which is incorporated herein by reference in its entirety) with an LOD score of 3.0. Standard errors for recombination frequency were determined according to Allard (Allard, R. W., *Hilgardia* 24: 235–278,1956; the content of which is incorporated herein by reference in its entirety). The primary genetic mapping experiment was reported by Wing, R. A., Zhang, H. B., & Tanksley, S. D. (*Mol. Gen. Genet.* 242: 681–688, 1994; the content of which is incorporated herein by reference in its entirety) and is described briefly below.

In order to map the jointless (j) locus using RFLP markers, an F2 mapping population, segregating for jointless, was generated from an interspecific F1 hybrid (*L.*

*Esculentum* j/j x *L. Pennellii* J/J). One hundred F2 plants were analyzed for segregation of the jointless phenotype to determine the penetrance of jointless in such a cross by scoring the presence or absence of a pedicel abscission.

Figure 4:
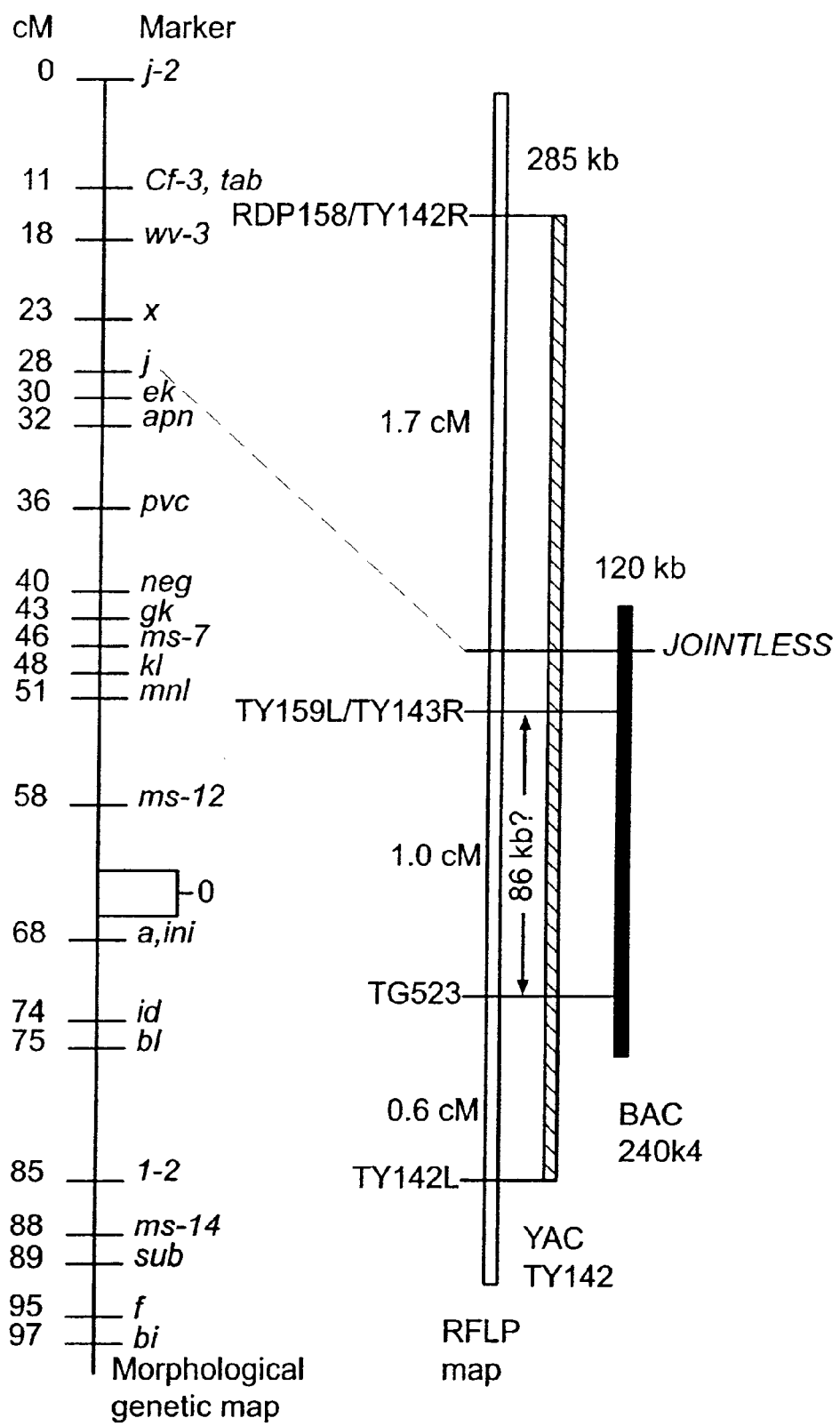
FIG. 4 is a schematic representation of a morphological map of tomato chromosome 11, a molecular genetic map, and YAC and BAC physical maps. The morphological map shows the location of jointless (j) between gametophyric factor (x) and elegans (ele). The molecular genetic map and physical maps, integrated with the morphological map with respect to the location of jointless (j), were generated from restriction fragment length polymorphism (RFLP) analysis and restriction enzyme mapping and sequence analysis of YAC and BAC clones, respectively, as described in Example 3.

Jointless was previously mapped to chromosome 11 between gametophyric factor (x) and elegans (ele) as illustrated on the morphological map shown in FIG. 4 (and see Rick, C. M. and J. T. Yoder, *Annu Rev Genet* 22: 281–300, 1988; the content of which is incorporated herein by reference in its entirety). When this mapping study was initiated, the morphological and RFLP maps had not been integrated. Only a single RFLP marker (TG105) was known to be linked to a gene on chromosome 11, the *Fusarium oxysporum* disease resistance gene 12 (Sarfatti et al., A RFLP marker in Tomato Linked to the *Fusarium oxysporum* Disease Resistance Gene I2, *Theor Appl Genet* 78: 755–759, 1989; the content of which is incorporated herein by reference in its entirety). Based on this information, several RFLP markers on the opposite arm of chromosome 11 were tested for linkage to jointless.

Figure 5:
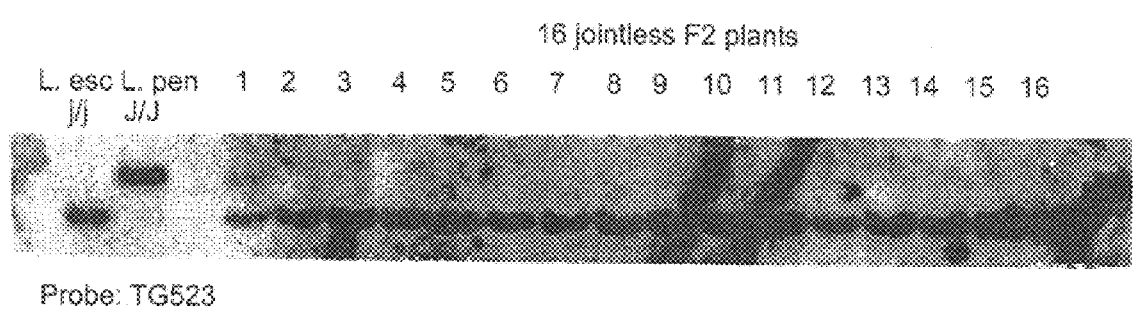
FIG. 5 is an autoradiograph of a Southern blot. DNA was isolated from 16 jointless $F_2$ progeny and probed with RFLP marker TG523.

FIG. 5 shows an autoradiograph of a Southern blot in which DNA isolated from 16 jointless $F_2$ plants was probed with a RFLP marker TG523. Of the 16 jointless F2 segregants (j/j), 15 exhibited the *L. esculentum* (jointless) RFLP pattern (lanes 5–19, plants 2–26), while one plant showed a heterozygous RFLP pattern (lane 4, plant 1).

The results of these studies indicated that TG523 was closely linked to jointless, which was mapped to a 7.1 (+/−1.8) cM interval between TG194 and TG523. TG523 was the most closely linked marker, mapping 1.5 (+/−2.0) cM from jointless. Further studies mapped another RFLP marker, RPD158, between jointless and TG194 flanking the jointless locus to 3.0 (+/−1.9) cM. FIG. 4 shows the RFLP map generated from RFLP analysis and integrated with the morphological map of tomato chromosome 11. Results of the mapping studies showed that one marker, RPD158, was the most closely linked marker to jointless opposite to TG523, mapping 1.5 (+/−2.0) cM from jointless.

Physical mapping As reported by Zhang, H. -B., Martin, G. B., Tanksley, S. D., & Wing, R. (*Mol Gen Genet* 244: 613–621, 1994; the content of which is incorporated herein in its entirety), a yeast artificial chromosome (YAC) contig encompassing the JOINTLESS locus was constructed and two YAC ends, TY159L and TY143R, were shown to genetically cosegregate with jointless, as is shown in FIG. 4. Jointless was determined to reside within approximately 100 kb of TG523, based on an estimated physical and genetic ratio of 86 kb/cM.

EXAMPLE 4

Tomato BAC Library Construction

The construction of a tomato bacterial artificial chromosome (BAC) library, previously described by Budiman et al. (*Genome Res* 10: 129–136, 2000; the content of which is herein incorporated by reference in its entirety) is briefly described as follows:

Genomic DNA preparation: A tomato BAC library was constructed from *Lycopersicon esculentum* cv. Heinz 1706 using a Hind III partial digestion of megabase-size DNA embedded in agarose plugs. To isolate tomato DNA, tomato nuclei were extracted and embedded in agarose plugs using the method adapted from DeScenzo and Wise (Variation in the Ratio of Physical to Genetic Distance in Intervals Adjacent to the Mla Locus on Barley Chromosome 1H, *Mol Gen Genet* 251: 472–482, 1996; the content of which is herein incorporated by reference in its entirety).

Briefly, chopped plugs were serially digested with Hind III (0 U, 0.5 U, 1.0 U, 2.5 U, 5.0 U and 50 U) in a total volume of 70 ul at 37 degrees Celsius for 20 minutes. After inactivating the restriction enzyme, partially digested fragments were separated by pulsed field gel electrophoresis (CHEF DR II, BioRad, USA). Three DNA fractions ranging from 100–150 kb, 150–200 kb, and 200–250 kb were excised. Gel pieces were washed three times with 1 ml of cold TE on ice for 10 minutes each and stored at 4 degrees Celsius prior to use.

BAC Vector Isolation: pBeloBAC 11 DNA (Shizuya et al., Cloning and stable maintenance of 300-kilobase-pair fragments of human DNA in *Escherichia coli* using F-factor-based vector, *Proc Natl Acad Sci* 89: 8794–8797, 1992; the content of which is herein incorporated by reference in its entirety) was isolated using an alkaline lysis method (Sambrook et al., Molecular Cloning: A Laboratory Manual, 2nd ed., Cold Spring Harbor Laboratory Press, Cold Spring Harbor, N.Y., 1989; the content of which is herein incorporated in its entirety). Vector DNA was purified by two rounds of CsCl density gradient centrifugation, completely linearized with Hind III (New England Biolabs, USA), and dephosphorylated with HK phosphatase (Epicenter Technologies, Madison, Wis.). The extent of digestion, dephosphorylation, and integrity of vector DNA were assayed by comparing several ligation reactions with Hind III cut Lambda (New England Biolabs, USA) on agarose gels and tested by transformation into *E. coli* DH10B (Research Genetics, USA).

Ligation: 50–150 ng of eluted tomato DNA and 20 ng of dephosphorylated linearized pBeloBAC11 vector were obtained. Before adding the T4 ligase (Promega, Madison, Wis.), the ligation mixture was incubated at 55 degrees Celsius for 10 min and then cooled to room temperature. Ligation was performed at 16 degrees Celsius overnight. One ul of the desalted ligation mixture was transformed with 20ul of *E. coli* DH10B (Research Genetics, USA) using a BRL electroporator. Transformed cells were spread onto LB media containing 12.5 ug/ml chloramphenicol, 50 ug/ml X-Gal 50, and 25 ug/ml IPTG and grown at 37 degrees Celsius for 18 hours. The clones on the plates were then picked with the Genetix Q-bot (Genetix LTD, UK) and stored in 384 well microtiter master plates containing LB freezing media (36 mM K2HPO4;13.2 mM KH2PO4; 1.7 mM sodium citrate; 0.4 mM MgSO4; 6.8 mM(NH4)2 SO4;4.4% glycerol (v/v); and 12.5 ug/ml chloramphenicol).

Library characterization: Inserts of most of the clones did not contain internal NotI sites which is a typical feature for dicot genomic DNA (Choi et al., Construction and Characterization of a Bacterial Artificial Chromosome Library from *Arabidopsis thaliana, Weeds World* 2: 17–20, 1995; Danesh et al., A Bacterial Artificial Chromosome Library for Soybean and Identification of Clones Near a Major Cyst Nematode Resistance gene, *Theor Appl Genet* 96:196–202, 1998; Marek, F. L. and R. C. Shoemaker, BAC Contig Development by Fingerprint Analysis in Soybean, *Genomics* 40: 420–427, 1997; the contents of which are incorporated herein by reference in their entirety). The average insert size was determined to be 117.5 kb. Seventy-eight percent of the clones had inserts greater than 100 kb. Approximately 11% of the clones contained inserts less than 70 kb, indicating that there were a significant number of small inserts (<100 kb) trapped in the size selected fraction used to construct the BAC library.

The entire library containing 129,024 clones was gridded onto seven 22.5×22.5 cm nylon filters (Hybond N+, Amersham, USA) using the Genetix Q-bot (Genetix Ltd., Dorset, UK). Each filter contained 18,432 individual clones that were doubly spotted. To determine the percentage of BAC clones containing chloroplast DNA in the library, high density membranes containing the entire library were probed with three chloroplast specific probes obtained from D. J.

Mullet (Texas A&M University, College Station, Tex.): ndhA of plasmid pBHP20, rbcL of pBPH134, and psbA of pBHE319, according to the hybridization procedure of Church and Gilbert (Genomic Sequencing, *Proc Nat Acad Sci USA*, 81: 1991–1995, 1984; the content of which is incorporated herein by reference in its entirety), except that bovine serum albumin (BSA) was omitted. The results showed that 1432 positive clones, representing only 1.11% of the entire library, contained chloroplast DNA sequences. Approximately 2.11% of the clones picked robotically were later found to be non-recombinant (blue) by inoculating clones from the first forty 384-well plates of the library onto petri plates containing X-gal and IPTG and counting the number of blue colonies (325 blue clones/15,360 clones). Taking into consideration that 1.11% of the clones contained chloroplast DNA and that 2.11% of the clones were non-recombinants, with an average insert size of 117.5 kb and a haploid genome size of 953 Mb, the library was estimated to contain approximately 15.4 haploid genome equivalents.

EXAMPLE 5

Sequence Analysis of a 120 kb Clone from Tomato Jointless Region

High-density hybridization filters containing 7.5 haploid genome equivalent clones, constructed as described in Example 4, were screened with TG523 which was located genetically within 1 cM (less than 86 kb) of the JOINTLESS gene. Results of the screening detected five positive clones. HindIII fingerprinting confirmed that these clones were overlapping.

A shotgun library was made from one of these clones, designated 240K4, which contained the largest insert (120 kb). DNA from 240K4 was isolated, sheared by nebulization under 6.5 psi nitrogen gas, end-repaired, ligated to pBluescript (Strategene, USA) and transformed into DH10B (Gibco-BRL, USA). Following transformation, three thousand clones were picked randomly and stored into 96-well microtiter plates, containing LB media and 20% glycerol, and grown overnight at 37 degrees Celsius. The plates were stored at −80 degrees Celsius.

Templates of shotgun clones were prepared by an Auto-Gen (Integrated Separation Systems, Japan) from 3 ml LB media incubated overnight at 37 degrees Celsius. DNA from each prep was isolated and dissolved in 80 ul water or TE. For sequencing, an ABI BigDye Cycle Sequencing Kit (Applied Biosystem Inc, USA) was used according to manufacturer's instructions with 4 ul of DNA. Sequencing was done on an ABI 377XL automatic sequencer according to manufacturer's guidelines. Twenty-six hundred clones were sequenced using sp10 primer (Operon, Inc., CA) according to the above procedure.

Sequences obtained as described above were uploaded to a Unix work station at Clemson University Genomics Institute (CUGI). The programs Phred and Phrap (Philip Green, University of Washington, Seattle, Wash.) were used to determine all the base sequence, cross match the vector sequences and assemble sequence contigs. The gaps between contigs were filled by performing another 400 sequencing reactions, using sp30, a reverse primer obtained commercially (Operon, Inc., CA), on clones located at the ends of each of the contigs. The 120 kb sequence of BAC 240K4 obtained above includes the genomic DNA sequence for JOINTLESS (SEQ ID NO: 1), and an extra 6 kb of vector pBeloBAC11. Vector DNA was identified by comparing the BAC 240K4 sequence to the vector sequence in the GenBank database. The sequence of JOINTLESS genomic DNA (SEQ ID NO: 1) was deposited in GenBank (Accession number AF275345).

EXAMPLE 6

Annotation of Genes Located on Tomato BAC 240K4

The 240K4 BAC sequence obtained as described in Example 5 was searched against the GenBank database for homology with known genes or genomic regions for full annotation. Coding regions were also predicted with the computer programs BlastN and BlastX, available through the National Center for Biotechnology (NCBI) website. Open Reading Frames (ORFs) were predicted by the computer programs Genescan (Stanford University, CA), BCM Gene Finder (Baylor University, TX), and Grail (Guan, X., R. J. Mural, J. R. Einstein, R. C. Mann, and E. C. Uberbacher, Grail: An integrated artificial intelligence system for gene recognition and interpretation, Proc, the 8th IEEE Conference on AI Applications, pp 9–13, 1992). The program Netplantgene (Hebsgaard et al., Splice site prediction in Arabidopsis thaliana pre-mRNA by combining local and global sequence information, *Nuc Acids Res* 24: 3439–3452, 1996) was also used to check the intron-exon borders when necessary.

The coding sequences and predicted proteins/peptides were searched against the databases. The Blastx search against Genbank sequences resulted in the identification of several homologous sequences. These include a *Pisum sativum* PsRT17 (240K4.9) which is a homolog of the tobacco Axi1 gene; a polyprotein of copia-like retrotransposon (240K4.11); a MADS-box gene (240K4.12); and two centromere-associated proteins (240K4.07 and 240K4.13). The newly-identified MADS-box gene 240K4.12 was putatively identified as the coding region for JOINTLESS (SEQ ID NO: 2, including the 5' and 3' non-coding regions, while SEQ ID NO: 3 depicts the nucleotide sequence of the coding region alone without the 3' and 5' non-coding regions). The sequences found most similar to BAC 240K4 are listed as follows:

TABLE 1

A List of Genes/ORFs on Tomato BAC 240K4

| Name*** | Coding region (aa) | Identified By | Best homology (GenBank*) | Best Blastp E value | TIGER EST** | Predicted Protein |
|---|---|---|---|---|---|---|
| 240K4.01 | 6701->831(489) | Genscan | T05632 | 2e-31 | | Putative permease |
| 240K4.02 | 12792->12499(97) | Genscan | No homology | | AW219175 | Unknown |

TABLE 1-continued

A List of Genes/ORFs on Tomato BAC 240K4

| Name*** | Coding region (aa) | Identified By | Best homology (GenBank*) | Best Blastp E value | TIGER EST** | Predicted Protein |
|---|---|---|---|---|---|---|
| 240K4.03 | 17218->16811(135) | Genscan | No homology | | | Unknown |
| 240K4.04 | 22769->26548(645) | Genscan | NP_009196 | 8e-90 | AW223638 | Suppressor of *S. cerevisiae* gcr2 |
| 240K4.05 | 27059->29336(251) | Genscan | AC006340 | 1e-68 | TC15929 | Unknown |
| 240K4.06 | 44765->39266(231) | Genscan | AAD22346.1 | e-160 | | Centromere protein |
| 240K4.07 | 50454->55443(1342) | Genscan | T05634 | e-120 | | Centromere protein |
| 240K4.08 | 57276->64326(660) | Genscan | P77253 | 8e-10 | AI487713 AI775878 | Probable membrane protein |
| 240K4.09 | 68613->66139(760) | Experiment | T06805 | e-105 | TC15287 | Probable growth regulator |
| 240K4.10 | 81558->80309(333) | Experiment | CAB80933 | 5e-51 | AI895494 | Unknown |
| 240K4.11 | 82164->86844(1441) | Genscan | BAA90383.1 | e-156 | TC14149 | Polyprotein of copia-like retrotransposon |
| 240K4.12 | 93143->89878(123) | Experiment | AAD22365 | 4e-75 | TC14213 | MADS-box transcription factor |
| 240K4.13 | 104149->109030(582) | Genscan | AJ001729 | 2e-25 | | TH65 protein |

*As done in April, 2000.
**TblastN homology > 90%;
***Genes/ORFS were predicted by Genscan. The approximate coding regions were determined also with reference to the Blastx results.

One ORF (240K4.12), homologous to MADS-box description factors known to control development of floral organs, was considered to be a strong candidate gene for JOINTLESS. To obtain definitive evidence that 240K4.12 was JOINTLESS, the presence of polymorphism at the jointless locus was investigated and the function of the MADS-box gene 240K4.12 was confirmed by complementation experiments, conducted as described in Example 9 below.

To determine if polymorphism existed at the jointless locus, the genome of the jointless homozygote (j/j) tomato line LA3023 was compared to that of the jointed homozygote LA3021 line. DNA was isolated from LA3023 and LA3021 as described in Example 2 above, and digested with the following restriction enzymes: BstN1, EcoR1, EcoRV, HindIII, and XbaI (Promega, Madison, Wis.). The digests were separated on a one-percent agarose gel and Southern blotted. The Southern blot was probed with a radiolabeled DNA fragment derived from the 240K4.12 open reading frame (ORF). The probe was PCR amplified with PCR primers MAOS-1 (5'-CAT TCT CCT CAA TCA TGA CTA A-3')(SEQ ID NO: 5) and MAOS-2 (5'-GGT TTA TTC TTT GTT CCC TC-3')(SEQ ID NO: 6) derived from that region. The PCR product was gel purified using a QIAEX II kit (Qiagen, USA) and labeled with $^{32}P$ using a DECAprimer II kit (Ambion Inc., USA).

Results from probing the Southern blots showed a polymorphism between the two tomato lines LA3023 and LA3021 and suggested a deletion in jointless region. The Southern blot results showed that the region carrying the suspected deletion in jointless tomato was about 1 kb shorter than that of the wild type. These results were confirmed with PCR and sequence analysis experiments.

Figure 6A:
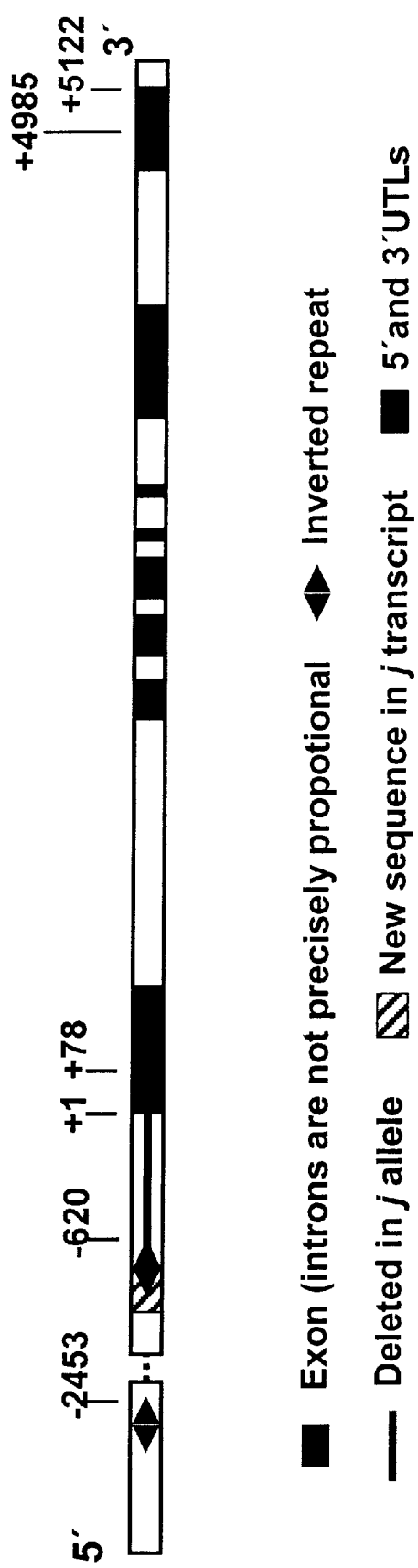

FIG. 6A schematically illustrates the wild-type JOINTLESS gene (from jointed tomato homozygote line LA3021). The transcription start point is designated as +1. Two inverted repeats (black arrows) are located at positions −620 and −2453, with the 939 base pair (bp) deletion occurring in the JOINTLESS allele involving the first inverted repeat.

FIG. 6B provides the genomic sequence of JOINTLESS (SEQ ID NO: 1), with exons depicted as lower case letters and the corresponding amino acid sequence appearing below the exons. Arrows indicate the start and end positions of an inverted repeat, while the deleted sequence in JOINTLESS allele is depicted in italicized letters. The polyA site is underlined and the stop codon marked as "*" The amino acids are conventionally designated, as follows: F: phenylalanine; L: leucine; I: isoleucine; M: methionine; V: valine; S: serine; P: proline; T: threonine; A: alanine; Y: tyrosine; H: histadine; Q: glutamine N: asparagine; K: lysine; D: aspartate; E: glutamate; C: cysteine; W: trytophan; R: arginine; and G: glycine.

Figure 7:
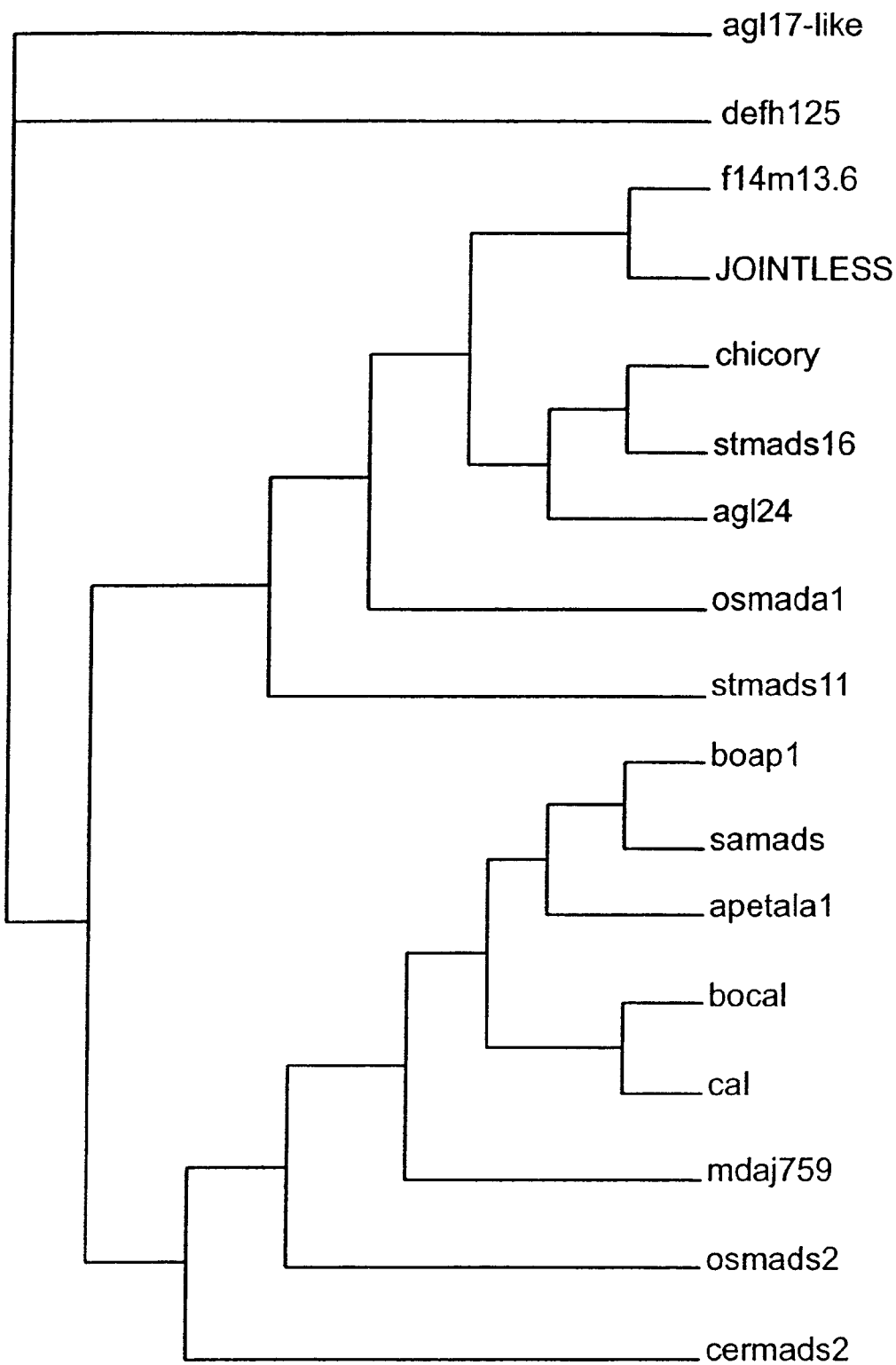
FIG. 7 is a phylogenetic tree generated from protein sequence similarities and shows JOINTLESS as located in a group distinct from MADS-box genes known to function in flower organs, such as the Arabidopsis cauliflower gene.

FIG. 7 is a computer-derived phylogenetic tree based on protein sequence similarity and constructed using the GCG computer program (Genetics Computer Group, WI). Results from the phylogenetic tree construction show JOINTLESS is located in a group distinct from MADS-box genes known to function in flower organs such as the Arabidopsis cauliflower gene.

EXAMPLE 7

Preparation of a Gene Transfer Cassette Containing Clone 240K4.12

Primers were designed according to the known exon regions and the estimated 5' leading sequence (promoter region) and used together with commercial T7/T3 primers (Operon, Inc., CA) whose sequences located on the vector used for cloning the cDNA (Chuang, 1997, Ph.D. Dissertation, Texas AM University; the content of which is herein incorporated by reference in its entirety). A PCR reaction was carried out from the phage lysate of the cDNA library without plating out. A fragment amplified with T7 and MAOS-p5 (a primer derived from the leading region having the sequence 5'-CCC TCT TTC TTC ATA ACT CTC TTA G-3' and designated as SEQ ID NO: 7) contained the coding region. Using T3 and MAOS-CD6 (5'-CTG AAG TTC AAG TGA TGG TTG GAT CC-3' and designated SEQ ID NO: 8) as primers, the 78 bp 5' region was obtained. The PCR products were cloned and sequenced and compared with the genomic sequence.

Sense and antisense cDNA constructs were made to complement the jointless tomato and to suppress the expression of JOINTLESS in jointed tomato, respectively. The full coding region was amplified using primers containing HindIII and XbaI sites and digested before purification. The digested PCR products were ligated to binary vector pBI121 (Gibco-BRL, USA) which was digested with the same restriction enzymes. The constructs were transformed into Agrobacterium strain LBA4404 (Life Science, USA).

EXAMPLE 8

Tomato Transformation Experiments

Tomato seeds from tomato lines LA 3023 and LA3021 were surface sterilized by soaking for 8 min in half strength of 5.25% sodium hypochlorite (commercial bleach), rinsing five times in sterile deionized water, and germinated at 23 degrees Celsius in a Magenta box containing 4.4 g/l MS salt (Gibco BRL, USA) (Murashige and Skoogs), 20 g/l sucrose, B-5 vitamins, adjusted to pH 6.10 (Gamborg et al., *Exp Cell Res* 50:151–158, 1968, the content of which is incorporated here by reference in its entirety).

Cotyledons from 11–13 day old seedlings were excised and gently cut with a #11#14 feather blade at both ends while immersed in 5 ml of liquid Agrobacterium (Gibco, USA) culture in a petri plate containing MSO agar co-cultivation medium (MS salts, B-5 vitamins and 14.7 mg of acetosyringone from Sigma, USA). Cotyledons were cut in half and precultured with Agrobacterium for 20–25 minutes, then placed 50–75 per plate and incubated for 48 hours.

Agrobacterium (LBA4404), containing a gene transfer cassette prepared as in Example 7, were grown for 2 days in 20 ml of YM (Gibco BRL, USA) liquid medium containing 50 mg/ml of kanamycin (Sigma, USA) at 30 degrees Celsius on a shaker. The culture was diluted 1:20 into fresh YM media and grown for 3 to 4 hours at 30 degrees Celsius on a shaker to produce a log-stage culture for inoculation.

After 48 hours on co-cultivation medium, the tomato explants were transferred onto selection/regeneration medium (consisting of MS salts, B-5 vitamins, 2 mg/ml of BA (Sigma, USA), 0.1 mg/ml of IAA (Sigma, USA), 50 mg/ml of Kanamycin, 500 mg/ml of carbenicillin at pH 6.0; as described by S. McCormick, *Plant Cell Reports* 5: 81–84, 1986; the content of which is incorporated herein by reference in its entirety).

Cotyledons or explants with nodular green callus/shoots were transferred to fresh selection/regeneration medium after 3 weeks in culture. After another 1–2 weeks, the shoots were excised at the base and transferred onto rooting medium consisting of MS salts, B-5 vitamins, kanamycin and carbenicillin as described-above.

Shoots rooted within 5–10 days or would bleach. Some shoots, which remained green but failed to root, were cut again at the base and transferred to fresh rooting selection medium to encourage root development. After 2–3 weeks, transgenic shoots with roots were transferred to potting soil (Lowes, Inc., SC) for further hardening and eventually transferred to the greenhouse.

Results of the transformation experiments for tomato cultivars LA3023 and LA3021 showed a transformation efficiency of approximately 30–35% as determined by the number of transgenic plants per explant obtained.

EXAMPLE 9

Tomato Complementation Experiments

Complementation experiments were performed to show that the transformation of jointless tomato plants (e.g. LA3023) with an expression cassette containing JOINTLESS candidate gene cDNA will restore the abscission zone and provide jointed progeny. Expression cassettes were constructed as detailed in Example 7. Cassettes were constructed with the cDNA in a sense orientation so the mRNA expressed will be the same as endogeneous one, therefore, the normal protein will be expressed later inside tomato plant. An anti-sense construct means the mRNA expressed in the transgenic plants will be complementary to the gene sequence or endogeneous mRNA. So, when antisense mRNA was expressed in the jointed tomato, the endogeneous mRNA was "blocked" because of the formation of double-stranded RNA and, therefore, lost its function as a template for translation—protein synthesis. This leads to the loss of the abscission zones in the jointed plants.

Tomato plants were transformed as detailed in Example 7 with either the cassette carrying the cDNA in a sense orientation or cassette with antisense cDNA. Transformation of the jointless tomato with the sense cassette resulted in primary plants (T0) which exhibited joints, while the jointed plants transformed with the cassette containing antisense cDNA were jointless at the flower pedicel in the T0 transformants.

Figure 8A:
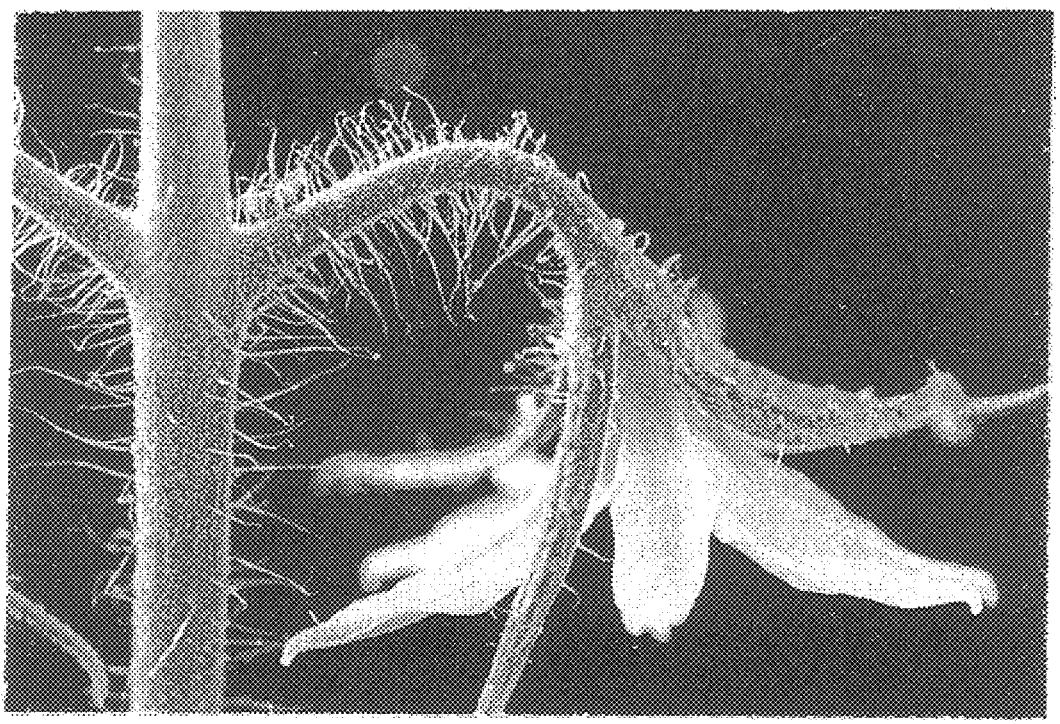
FIGS. 8A–8F are photographs showing the results of complementation experiments described in Example 8.
Figure 8B:
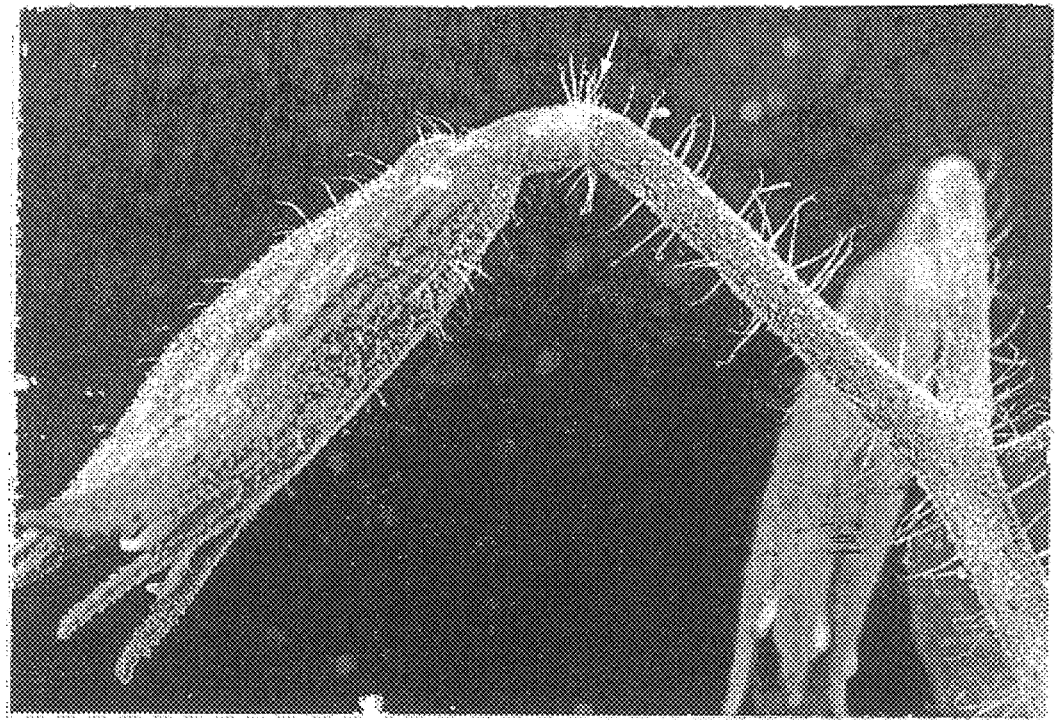
Figure 8C:
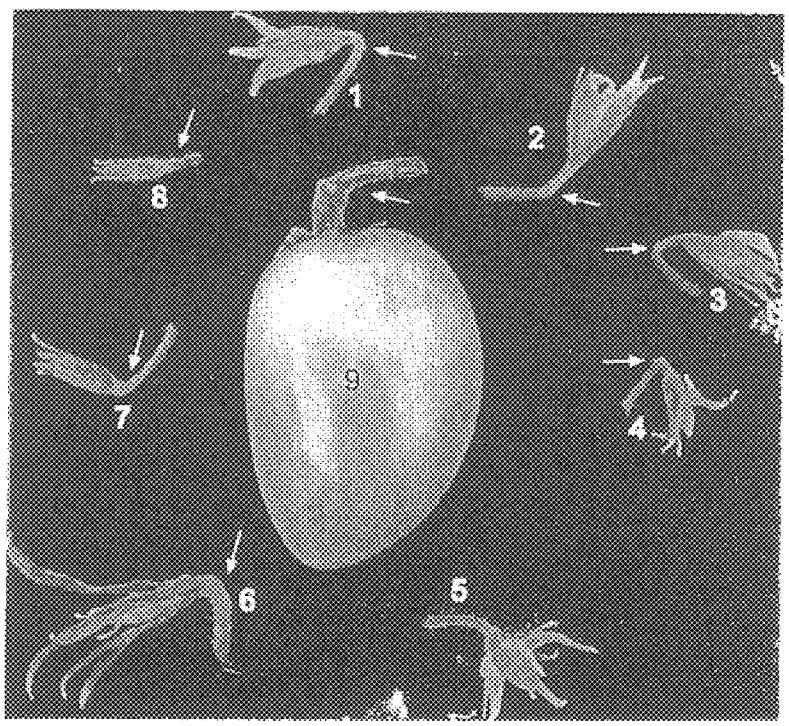
Figure 8D:
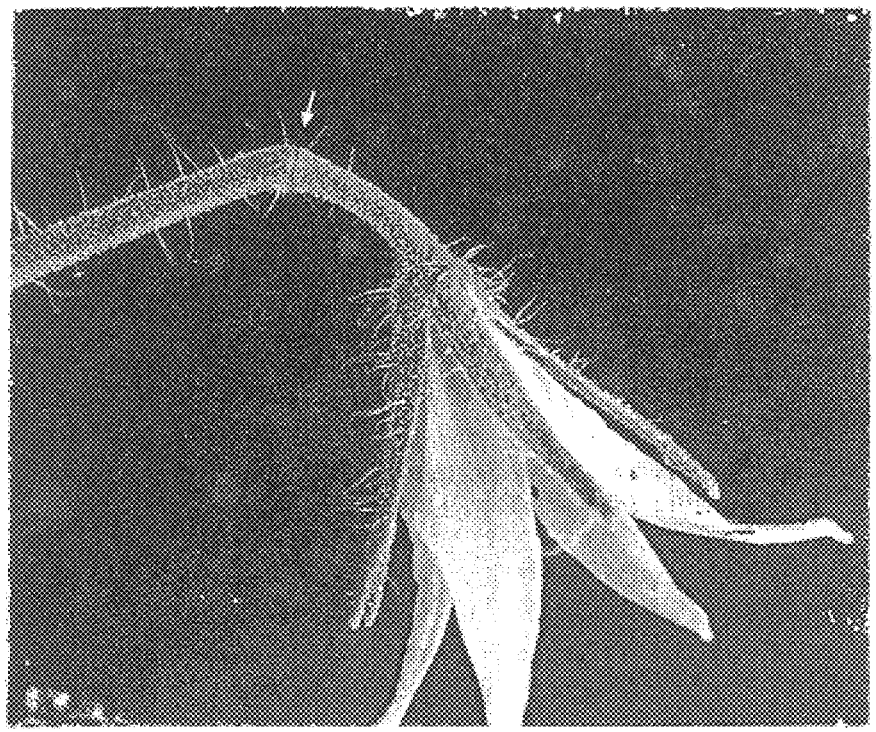

FIGS. 8A–8F are photographs illustrating the results of the complementation experiments described above. FIG. 8A is a photograph of a flower from the jointless control (LA3023), while FIG. 8B shows a flower with a rescued AZ on its pedicel from a jointless plant transformed with a sense construct. Note that the position of the AZ on the pedicel is closer to the flower than those on the wild-type pedicel from jointed control plant LA3021, as shown in FIG. 8D.

FIG. 8C shows various flowers/fruit from sense rescued jointless plants. The putative rescued AZ or AZ-like structures are slightly yellowish regions on the pedicels. Flower 5 is from a jointless T2 progeny and shown as a control. Flowers 1, 2, 3, 4, and 9 were from primary sense plants, while flowers 5, 6, 7, and 8 were from T2 progeny of a primary sense transgenic plant.

Figure 8E:
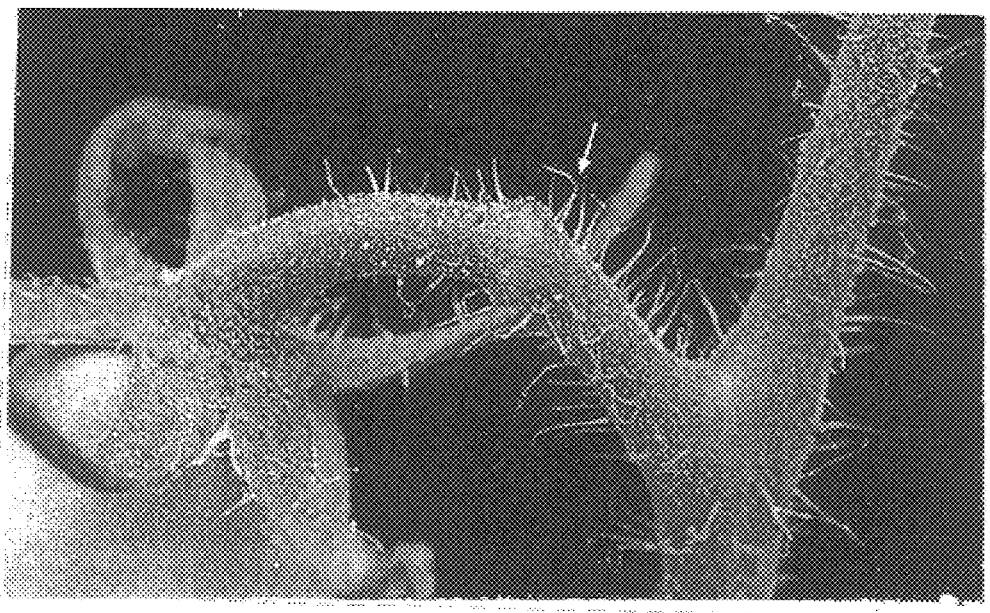

FIG. 8E is a photograph illustrating a partially suppressed pedicel caused by an antisense transgene. The bump-like structure is supposed to be at the position of original AZ in wild-type tomato.

Figure 8F:
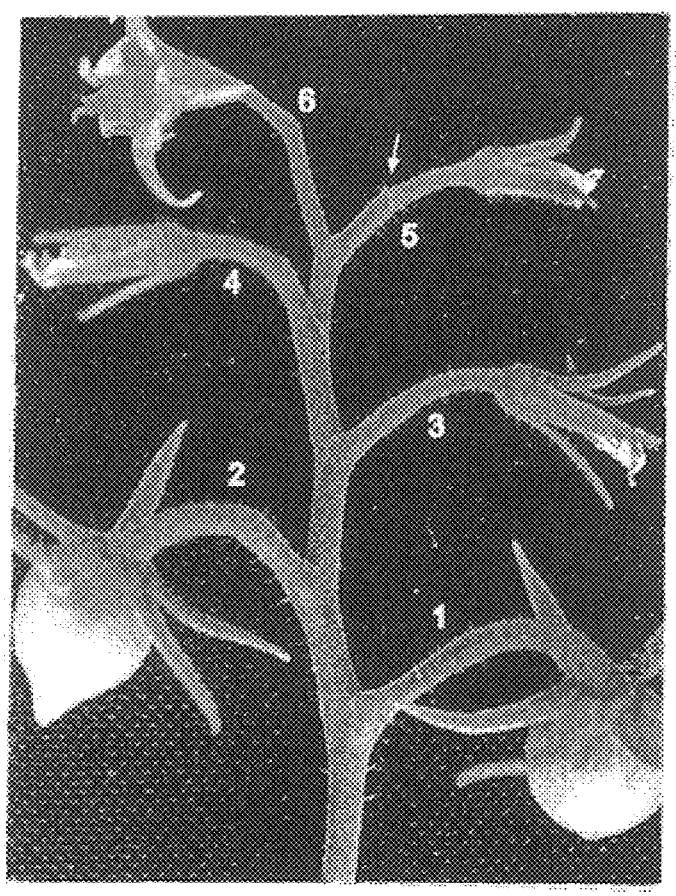

FIG. 8F shows the gradual reversion of suppressed AZs on the same inflorescence from an antisense transformed wild-type tomato plant. Complete suppression of AZ development in flowers 1, 2, and 3 is shown clearly, however, a bump-like structure appeared on the pedicel of flowers 4 and 6. Flower 5 has almost an AZ-like structure on its pedicel.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

We claim:

1. An isolated nucleic acid comprising a nucleotide sequence that hybridizes to a hybridization probe having the polypeptide coding sequence of SEQ ID NO: 1, or a complement or degenerate variant thereof, wherein the isolated nucleic acid comprises a nucleotide sequence at least 95% identical to a nucleotide sequence selected from the group consisting of SEQ ID NO: 1, SEQ ID NO: 2 and SEQ ID NO: 3, and wherein the isolated nucleic acid encodes a polypeptide capable of producing an abscission zone in a plant.

2. The isolated nucleic acid of claim 1, wherein the nucleotide sequence that hybridizes to the hybridization probe has the nucleotide sequence SEQ ID NO: 1, or a complement or degenerate variant thereof.

3. The isolated nucleic acid of claim 1, wherein the nucleotide sequence that hybridizes to the hybridization probe has the nucleotide sequence SEQ ID NO: 2, or a complement or degenerate variant thereof.

4. The isolated nucleic acid of claim 1, wherein the nucleotide sequence that hybridizes to the hybridization probe has the nucleotide sequence SEQ ID NO: 3, or complement or degenerate variant thereof.

5. The isolated nucleic acid of claim 1 wherein the plant is a tomato plant.

6. The isolated nucleic acid of claim 1 comprising a nucleotide sequence at least 95% identical to SEQ ID NO: 1, or a complement or degenerate variant thereof.

7. The isolated nucleic acid of claim 1 comprising a nucleotide sequence at least 95% identical to SEQ ID NO: 2, or a complement or degenerate variant thereof.

8. The isolated nucleic acid of claim 1 comprising a nucleotide sequence at least 95% identical to SEQ ID NO: 3, or a complement or degenerate variant thereof.

9. The isolated nucleic acid of claim 1, wherein the isolated nucleic acid is isolated from a tomato plant.

10. The isolated nucleic acid of claim 1, wherein the isolated nucleic acid is a vector comprising a nucleic acid having the nucleotide sequence SEQ ID NO: 3, or a complement or degenerate variants thereof.

11. The isolated nucleic acid of claim 10, wherein the vector is an expression vector.

12. The isolated nucleic acid of claim 11, wherein the expression vector comprises the isolated nucleic acid having the nucleotide sequence SEQ ID NO: 3, or a complement or derivative thereof, and operably linked to an expression control sequence.

13. The isolated nucleic acid of claim 1, wherein the isolated nucleic acid has the nucleotide sequence SEQ ID NO: 3, and wherein the nucleic acid is operably linked to a heterologous nucleic acid.

14. The isolated nucleic acid of claim 13, wherein the heterologous nucleic acid is selected from the group consisting of a promoter, an enhancer and a transcription activator.

15. A cultured cell comprising the recombinant vector of claim 10.

16. A cultured cell, or a progeny cell thereof, comprising the recombinant vector of claim 10, wherein the cultured cell and the progeny cell thereof are capable of expressing a polypeptide encoded by the vector, and wherein the polypeptide is capable of producing an abscission zone in a plant.

17. The cultured cell or a progeny cell thereof, of claim 16, wherein the polypeptide has the amino acid sequence SEQ ID NO: 4.

* * * * *

SEQUENCE LISTING

<160> NUMBER OF SEQ ID NOS: 4

<210> SEQ ID NO 1
<211> LENGTH: 6701
<212> TYPE: DNA
<213> ORGANISM: Lycopersicon esculentum

<400> SEQUENCE: 1

```
tatttcatat taattgtcca tattgctcaa ataattatt ctaaattatt gtcaaactta      60
caaaccaca ataaaattaa ttatattacc cccccccccc tattttctca ttaataacaa     120
ttcttttaa aagtgtaaaa ttttaaaaat aaaataaaat attaaaagaa ataaataagt     180
aaacccccc ttcttattag tgattataca taaattacaa acaattaaat ataagacgat     240
aaaaatatct aacacataat aaaattaatc aaaatacaca taatctaatt tttaaataca    300
ttataaaatt aatcaaaata tacacaacct aacttctttc attctttgcc taatataaac    360
acaatctcta taattagaaa cttttgccta tctacccccc accccaccca cccaccccctc   420
tctacaatta ggtcatcaca cacacaaaca tttctttgta ttctggttta ttctttgttc   480
cctcttttat aaattccctc tttcttcata actctcttag ttctattttt ggaaaattaa   540
aaaaaaaaaa actcctaatg gctagagaaa aaattcagat caagaaaata gataactcca   600
cagcaagaca agttacattt tcaaagagga gaagaggttt attcaagaaa gctgaagaac   660
tttctgttct ctgtgatgct gatgttgctc tcatcatttt ctcttctact ggaaaattat   720
ttgactattc tagctcaagg tacatatcca tcattttttc tttcatttac ctaattataa   780
cgacagcaac atactcagtg aaattccggg acccgaaaag aatagtaggt gtatgtaaaa   840
tcacctaatt atccttattt tttgtttgtg gtagctagat tagttgtttt ctagactaaa   900
aaaaagaaat tgggaataat ttttgattag ttattaaata ataacgtatt tagtaaaatt   960
ttagaaatga attttgagta aagtgatgtg tatgtgtatt ttatctatag ggtagagagg  1020
ttttttccga tgaattttag ggctaattta acaagtgaaa attaaagtaa tgatttttgt  1080
taattttttg tgaggaatga agttttttt tttttttttgg gtattttcta aatgggtgac  1140
tttagttagt catgattgag gagaatgatt agaattattg agttttggat ttttgtaaat  1200
atagtttatt aattaattat tatattaaat ggattttttag gtataaattt agggtttgat  1260
tttaagttat tgagttttgt tgaattctta ggaaaagttc ttcgctgttg tttacaaatg  1320
ggtgtcttta agctagtcat gattgacaag aattatatcg agttatttaa attctgaaag  1380
aagattttga taaattgttt atatatgtaa aaagtgagat tttataatat aaatttaaaa  1440
atttgatcaa aagctattag atttcatcgt gcccgcatac aaatctcttc tctattattt  1500
aacaagttat gtgcactgat aatattacta atatacttta atttgttata ataccaatta  1560
agttacatag tttaatttgt gtagaagtta agttactact tttgtcaagt aatttactta  1620
ttaattacta catggttttc acataacata aacacttgct atatttagca actattgaga  1680
aacccacctc aagaaacttt ctattttgtg tcatttattg actctttttt ttaggtaaat  1740
aattaatgaa aaaaacttga attttgtatt agaaacaaa gcttctaaag actcaatttt  1800
tatttaaaaa ggaatcagaa aaaatggaga ataaacaata ataccaacac aaaatgagtg  1860
```

-continued

```
gtgtaggaag tagttagtag ttaccaggtt ataagaattt tatgttgttt aaattcttca    1920
aaaatattat tacattatat tagatcattt tataacatgt agtaatttt gatgatttga     1980 tgtgtcaatg taaattttat tcttttggat tgaaaatata tattttcgca cacaatgaca    2040
ttattaaagg attcacagaa tatatatgtc aatttcattt atgaaattca aaattttgt     2100 tacattatta attaaattga cttgtaataa caaataatat tttaaagctt agatagaaca    2160
ataaaaaaat aaaagggaat aaatttagct ggataatgtt atcgaaaggg ccaccatatc    2220
ttatctgttt cacagaaagg caataatatt atatcttata atataaaaat aaatattatc    2280
atgggaacta tatatttatg gtgaatagga caaactcctt ttaatgggga aaaaagaag     2340 catattttag gaattttatg ttttttttt gtatggtata agtaaaaagt aacaaatttg      2400
atgagctatt ttttgaggt ggttgtgtgt ggtatataaa ataattgttt tcccctcta       2460 caagtaaatg ttttaagaaa gctataatga actctcttca ttcggtattg tttgtcataa    2520
tttttatttt tagagttaaa ttatgaaaat tttgacttac attttaagat gtattttta     2580 atcatattaa tatgtaaaaa attgtaattt atagtatttt ccatataatt ttaggatatc    2640 taatttttt gtttaaaata tcgaattaat ctgatctaat ttacctttga aaattaatca      2700 agtgactta gataagtgca tcatgataaa caattccgga cgaagggtgt ataattaatc      2760 tacatttaa taatttgatt ttttttttat aattcactta tttatcatcc tcgatattta      2820
agcttattga gtgtgtcata tatcaaagat taatagatcg tcttttata gtcttgaata     2880 atcttatact tcataggttt attacttttg aagttgagtc agacttatcc ttagctatta    2940
gtattatgtc gttaagttga taggcctgct cgaatgggga agaggtgtta tctatcccac    3000
attagttgac ggatgagttg tttatgtcgg tgttaagcaa tattttcat ttgagattga     3060 gttagatcta aagtcaattt tctcgacaga aattacaaat ttgtctttta ctttctttga    3120
tgttgtgttc atgtgtccct aatatattgg atacatgaca catacataca ttcttcaaag    3180
gaatttaata tttatgtatg tatcgacatc ataattgatc acataaaaga taactatata    3240
taattctacc gttcatcaat gatttacgta cgatcttaat attttaatt tctcatgaag      3300 catgaaacaa attcttgaga ggcgtgattt gcattccaaa aatctggaaa aattggatca    3360
accatcactt gaacttcagg taattaattc atttatttaa tccttaatta cattttaatt    3420 agttttaaa caaatatttt gtttatttg tttgcagctt gtagaaaata gcaactactc       3480
cagattaagc aaggaaattt ccgaaaaaag tcatcgatta aggtatattt atagttacat    3540
ttgaaatcga ctatatgtat tctcactgtt cttttagtt caattcataa tatccatcat     3600
cacatacgtc aaacaaaagt aaaagagaga caagttaatt tatatatata tatatata     3660 tataaaaaat tacgataata ataataatat tagaagttct ctaacaagta gcatcgatta    3720
acaggcaaat gagggagaa gaacttcaag gactaaaatat tgaagagttg caacaattgg    3780
agagatctct tgaaactgga ttgagccgcg tcatagagag aaaggtcggg attaacttaa    3840
tatatattga cattataaaa tatatttat gttattagtg taatttaata tgtcgtaaca     3900
agttataatc gattttccc cttttaata tcttacacaa cttacgttat ccatgtatca       3960
gggtgataaa ataatgagag agatcaacca actccaacaa aaggtaggaa acaatatcgt    4020
ttaagtgatc tggtagtgta taatttttgt atcgcaattt tacttggttt tcatcgacgc    4080
tgataattgt tattgtgaaa atcaacagg gtatgcatct aatggaagaa aatgaaaaat     4140
taaggcaaca ggtatgcaaa ttttttaacg aatgagataa aaattgatta ttttactata    4200 atttagata gccggtgatt actgaaatct ccgagacatc aggttgaaat ttcaataaaa      4260
```

-continued

```
tctatgaatt tgtagatgat tttttcctat ttccgaaatc tccgaaaaac ttaagctttt    4320
taaaattaac ttttttatgg atacacttgg agtatctaaa ttattcaaga cttcaataat    4380
tatgttatta aatgttatcg ttgatatata ttttttaattt ttttaggtg atggagatat    4440 ctaataataa taataataat aataatggat atagagaggc aggagtagta atatttgaac    4500
cagaaaatgg atttaataat aataataatg aagatggcca atcatctgaa tcagtaacaa    4560
atccatgtaa ctcaattgat cctcctcctc aagatgatga tagttctgat acttctctca    4620
aattggggtt agtactttaa ttctttcttc ttcttttttc cggtctcgtt tcgatctcgt    4680
ttcgtatgaa agataaaaga aattattaat ttcaatttta attttgtgaa gaaataatct    4740
attttgaatt gttgtgttgt ttgttttttaa tactgaaggc ggaataatga ttttagaga    4800 acttatccta gaattatttt gagataactt attttccgtt caaacgaatt gtggtcgtga    4860
aaaaatattc gtttatcaat acactattgg taaattgtat atcaagtatc taccttctga    4920
aggtgttgca tacatattac ccttttttaaa ctttacttcg gtatcatgtt attgtatatt    4980
gtttatgtaa agggacaaca aaagttaggg gctaatcgag ttcagtaatt ttgactcaaa    5040
tatgatattt gtgggttaaa tttttttatg aatatttat tatcgaaagt agaagtcttt    5100
gtacggattt gaatgaacca aatatcttta gttcatatct ttgtattggt atttagaata    5160
ctcataaata tgtacatttt ttttttaatt caaaacctcg ttactaaccc ttgatgttgt    5220
tatcttaaaa tttagaacgt atacgtaata tttaaatttc aactctgttc tataggttca    5280
ccttcatgtt ctaaatttat aacccataat acataaattt aaaattctga gtccgtttct    5340
gatattatat tttttttcat cttatttgtt tttaaaatgt caggctacct tactcaggct    5400
gaagagatca aaagcaaggt gtggctattt ttgtatgtta ttagaagaag gagaaaaaaa    5460
aaagtaacta ctaattatta taattaatta atgtctgatt aatgtaaaag ctaaccccaa    5520
aaatttcata ttatgtatgt aattggtgta ttaatctcat gtattcgtct cccatagttt    5580 atataaaatat tattgttagt atctattaac ttaattaact agcactaata atctttata    5640 attgaacttt gtgacttgta actatataaa ggcttaatta tttaattatt tgactttttt    5700
ctgttgctgt aaatttaaat atttacttgg tgacggtaaa ctatacttct atctatattc    5760
agtgttgaac attagttatt tgaaattttt agtggatgat ttataatatg ttattgtaag    5820 ataatttaa tttaattttt tgaatcattt ccgtatctag cactaattaa tttgtagtcc    5880
ttatcatgtt catatttaat agttgaagac atgcataaaa acaattcaat tacttgagtt    5940 tcatttcaa accattaggt tgtatatgtt tcttatccaa attataataa atcatttata    6000
gaaattttaa cacaattatt atgtgtgtac gttttttaatt tttttttaatc aaaatacacc    6060 ttaactataa ggagtgtgag ctttctaaac tatttaccaa aacacatttc aactatcaaa    6120
tgtaccgatt tttttttatct aaaataggaa aaaacttacc cgcagaatgt ttacatcaaa    6180
gtcaatgcaa tttccgttat tatgtaattt aatgaagtaa aatgaataat aaatttcaac    6240
acatgacata catatattga cagtgtaaat cttcgacgtg gttttacccc taaaatatta    6300
tcatcatttg agtaaaaaga taacaatatt cgatacttga tatacctttt aaaaaaatca    6360
aaactgttgc aaagaaagct cagaatataa gaagaaaagg acaagaagta taagatagag    6420 gagataatttt tcttattcaa gtatgtatta caaaaggtga atgatatctc tatttataga    6480
gttgagatat caccccaaaa gccccccatga taaatgtcca attagtaggt acatagttat    6540
ccaaatgatt cttatcacct tgggaacatg tatacatgaa tacaattaag tcttgagtaa    6600
```

```
atctaaagga taatccacac aatccaatgg atttataaca cttcccttg gatgtccata      6660 gattatgtgc ctcgttaaaa ccttactagg aaaaacccag t                         6701

<210> SEQ ID NO 2
<211> LENGTH: 1010
<212> TYPE: DNA
<213> ORGANISM: Lycopersicon esculentum

<400> SEQUENCE: 2
ccctctttta taaattccct ctttcttcat aactctctta gttctatttt tggaaaatta       60
aaaaaaaaaa aactcctaat ggctagagaa aaaattcaga tcaagaaaat agataactcc      120
acagcaagac aagttacatt ttcaaagagg agaagaggtt tattcaagaa agctgaagaa      180
ctttctgttc tctgtgatgc tgatgttgct ctcatcattt tctcttctac tggaaaatta      240
tttgactatt ctagctcaag catgaaacaa attcttgaga ggcgtgattt gcattccaaa      300
aatctggaaa aattggatca accatcactt gaacttcagc ttgtagaaaa tagcaactac      360
tccagattaa gcaaggaaat ttccgaaaaa agtcatcgat taaggcaaat gaggggagaa      420
gaacttcaag gactaaatat tgaagagttg caacaattgg agagatctct tgaaactgga      480
ttgagccgcg tcatagagag aaaggggtgat aaaataatga gagagatcaa ccaactccaa      540
caaaagggta tgcatctaat ggaagaaaat gaaaaattaa ggcaacaggt gatggagata      600
tctaataata ataataataa taataatgga tatagagagg caggagtagt aatatttgaa      660
ccagaaaatg gatttaataa taataataat gaagatggcc aatcatctga atcagtaaca      720
aatccatgta actcaattga tcctcctcct caagatgatg atagttctga tacttctctc      780
aaattggggt tagctacctt actcaggctg aagagatcaa aagcaaggtg tggctatttt      840
tgtatgttat tagaagaagg agaaaaaaaa aagtaactac taattattat aattaattaa      900
tgtctgatta atgtaaaagc taaccccaaa aatttcatat tatgtatgta attggtgtat      960
taatctcatg tattcgtctc ccatagttta tataaatatt attgttagta                1010

<210> SEQ ID NO 3
<211> LENGTH: 798
<212> TYPE: DNA
<213> ORGANISM: Lycopersicon esculentum

<400> SEQUENCE: 3
atggctagag aaaaaattca gatcaagaaa atagataact ccacagcaag acaagttaca       60
ttttcaaaga ggagaagagg tttattcaag aaagctgaag aactttctgt tctctgtgat      120
gctgatgttg ctctcatcat tttctcttct actggaaaat atttgactat ttctagctca      180
agcatgaaac aaattcttga ggcgtgatt tgcattccaa aaatctggaa aaattggat      240 caaccatcac ttgaacttca gcttgtagaa aatagcaact actccagatt aagcaaggaa      300
atttccgaaa aagtcatcg attaaggcaa atgagggag aagaacttca aggactaaat      360
attgaagagt tgcaacaatt ggagagatct cttgaaactg gattgagccg cgtcatagag      420
agaaagggtg ataaaataat gagagagatc aaccaactcc aacaaagggg tatgcatcta      480
atggaagaaa atgaaaaatt aaggcaacag gtgatggaga tatctaataa taataataat      540
aataataatg gatatagaga ggcaggagta gtaatatttg aaccagaaaa tggatttaat      600
aataataata atgaagatgg ccaatcatct gaatcagtaa caaatccatg taactcaatt      660
gatcctcctc ctcaagatga tgatagttct gatacttctc tcaaattggg gttagctacc      720
ttactcaggc tgaagagatc aaaagcaagg tgtggctatt tttgtatgtt attagaagaa      780
```

```
ggagaaaaaa aaaagtaa                                                    798

<210> SEQ ID NO 4
<211> LENGTH: 265
<212> TYPE: PRT
<213> ORGANISM: Lycopersicon esculentum

<400> SEQUENCE: 4

Met Ala Arg Glu Lys Ile Gln Ile Lys Lys Ile Asp Asn Ser Thr Ala
1               5                   10                  15

Arg Gln Val Thr Phe Ser Lys Arg Arg Gly Leu Phe Lys Lys Ala
            20                  25                  30

Glu Glu Leu Ser Val Leu Cys Asp Ala Asp Val Ala Leu Ile Ile Phe
        35                  40                  45

Ser Ser Thr Gly Lys Leu Phe Asp Tyr Ser Ser Ser Met Lys Gln
    50                  55                  60

Ile Leu Glu Arg Arg Asp Leu His Ser Lys Asn Leu Glu Lys Leu Asp
65                  70                  75                  80

Gln Pro Ser Leu Glu Leu Gln Leu Val Glu Asn Ser Asn Tyr Ser Arg
                85                  90                  95

Leu Ser Lys Glu Ile Ser Glu Lys Ser His Arg Leu Arg Gln Met Arg
                100                 105                 110

Gly Glu Glu Leu Gln Gly Leu Asn Ile Glu Glu Leu Gln Gln Leu Glu
                115                 120                 125

Arg Ser Leu Glu Thr Gly Leu Ser Arg Val Ile Glu Arg Lys Gly Asp
    130                 135                 140

Lys Ile Met Arg Glu Ile Asn Gln Leu Gln Gln Lys Gly Met His Leu
145                 150                 155                 160

Met Glu Glu Asn Glu Lys Leu Arg Gln Gln Val Met Glu Ile Ser Asn
                165                 170                 175

Asn Asn Asn Asn Asn Asn Gly Tyr Arg Glu Ala Gly Val Val Ile
                180                 185                 190

Phe Glu Pro Glu Asn Gly Phe Asn Asn Asn Asn Glu Asp Gly Gln
        195                 200                 205

Ser Ser Glu Ser Val Thr Asn Pro Cys Asn Ser Ile Asp Pro Pro Pro
    210                 215                 220

Gln Asp Asp Ser Ser Asp Thr Ser Leu Lys Leu Gly Leu Ala Thr
225                 230                 235                 240

Leu Leu Arg Leu Lys Arg Ser Lys Ala Arg Cys Gly Tyr Phe Cys Met
                245                 250                 255

Leu Leu Glu Glu Gly Glu Lys Lys Lys
                260                 265
```